Figure 1:
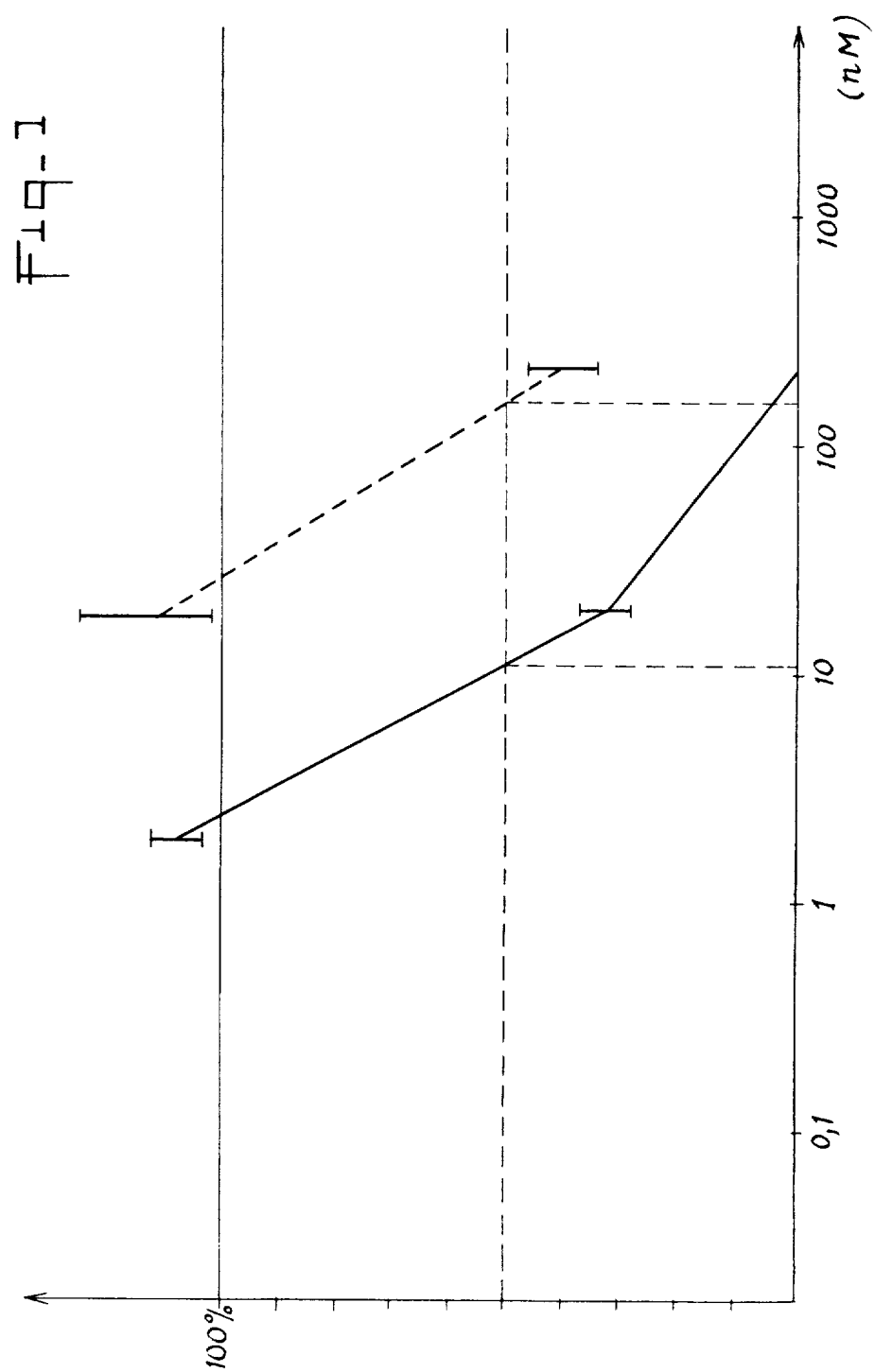

United States Patent [19]

Voisin et al.

[11] 4,340,535

[45] Jul. 20, 1982

[54] CYTOTOXIC PRODUCTS FORMED BY COVALENT BONDING OF THE A CHAIN OF RICIN WITH AN ANTIBODY AND THE PROCESS FOR THEIR PREPARATION AND USE

[75] Inventors: Guy Voisin, Paris; Franz Jansen, Saint Gely Du Fesc; Pierre Gros, Montpellier, all of France

[73] Assignee: C M Industries, Paris, France

[21] Appl. No.: 79,441

[22] Filed: Sep. 27, 1979

[30] Foreign Application Priority Data

Sep. 28, 1978 [FR] France ................................ 78 27838

[51] Int. Cl.³ ........................ A61K 39/44; C07G 7/00

[52] U.S. Cl. ............................ 260/112 B; 260/112 R; 424/85

[58] Field of Search ....................... 260/112 R, 112 B; 424/85

[56] References Cited

U.S. PATENT DOCUMENTS

| | | | |
|---|---|---|---|
| 4,046,722 | 9/1977 | Rowlands | 424/85 X |
| 4,093,607 | 6/1978 | Sela et al. | 260/112 B |

OTHER PUBLICATIONS

Annals of the N.Y. Acad. of Sciences, 277, 690–699, (1976), Moolten et al.

*Primary Examiner*—Howard E. Schain

*Attorney, Agent, or Firm*—Brooks, Haidt, Haffner & Delahunty

[57] ABSTRACT

Carcinostatic products are formed by coupling, by covalent bonding, the A chain of ricin with an antibody which is capable of selectively recognizing a given antigen at the surface of cancerous cells. Such products can be made by the formation of a disulphide bridge between the free thiol group in the A chain of ricin and an immunoglobulin or immunoglobulin fragment into which a thiol group or an activated disulphide group has been introduced. The A chain of ricin and the immunoglobulin are carefully purified before use.

14 Claims, 8 Drawing Figures

CYTOTOXIC PRODUCTS FORMED BY COVALENT BONDING OF THE A CHAIN OF RICIN WITH AN ANTIBODY AND THE PROCESS FOR THEIR PREPARATION AND USE

DESCRIPTION

For many years, the treatment of cancer has given rise to multifarious research. More particularly, a very large number of substances have been proposed for the cheomotherapeutic treatment of cancer by the more or less selective destruction of the cancerous cells. Although it has been possible to achieve certain results, the chemotherapy of cancer is restricted by the nonspecific toxicity of the antineoplastic agents towards normal high-growth cells such as, for example, the stem cells from blood lines. As a result, the effectiveness of the treatment is inadequate to permit the removal of the last cancerous cells, which cells will subsequently cause new growths of cancer.

In order to reduce the toxicity of carcinostatic agents towards normal cells, various experiments have been carried out [see in particular: C. R. Academie des Sciences de Paris 246, 1,626 (1958); British Medical Journal 3, 495 (1972); Science 169, 68 (1970) and Cancer Research 35, 1,182 (1975)]. The aim of these experiments was to couple molecules having a cytotoxic activity with antibodies directed against the cancerous cells, in order to fix them solely to the target cells. However, in practice, these experiments have not achieved notable results, essentially because the cytotoxic substance carried by the antibody remained active during its transfer into the organism and was able to inhibit the growth of normal cells before encountering the cancerous cells.

The present invention relates to active substances for the treatment of cancer, which consist of a cytotoxic agent coupled to an immunoglobulin which is specific for cancerous cells. These substances exhibit the characteristic that they remain inactive during their transfer and only become active after fixation to the target cells and penetration into these cells. The immunoglobulin used can be an antibody which is specific for a given antigen or can also be a fragment of this molecule, which possesses the capacity of specific recognition with respect to the antigen, such as, for example, the fragments which are usually denoted by the name Fab, F(ab)' or F(ab')₂. As regards the cytotoxic substance, the A chain of ricin seems to constitute a very valuable substance.

In fact, it is known that ricin, which is a toxic lectin extracted from the seeds of Ricinus communis, consists of the association of two polypeptide chains by means of a disulphide bridge. The A chain, or "effectomer", has an intense cytotoxic activity by virtue of the inhibition of protein synthesis in the cells of eukaryotes. However, this A chain does not possess the property of effectively penetrating into the cells to exert its biological activity therein. Furthermore, the B chain of ricin, or "haptomer", possesses the property of recognizing saccharide units at the surface of the cells, with which units it creates an association of high affinity. Natural phenomena then make it possible to cause the ricin molecule to penetrate into the contents of the cell, where the A chain exerts its toxic activity. The toxicity of ricin is devoid of any specificity with respect to a particular type of cell, insofar as virtually all animal cells carry saccharide determinants which are recognised by the B chain.

The aim of the present invention is to produce artificial hybrid molecules, denoted by the term "conjugates", in which the A chain of ricin is associated by means of a suitable covalent bond, preferably of the disulphide type, not to the B chain but to a protein structure which is capable of selectively recognising a given antigen at the surface of the cells carrying this antigen. As indicated above, this protein structure will be an immunoglobulin which is specific for the desired antigen, or any fragment of this immunoglobulin which possesses the same specificity of recognition.

The choice of the A chain of ricin as the cytotoxic constituent of the conjugates mainly results from the following facts:

an extremely high level of cytotoxic activity when, and only when, the A chain has penetrated into the contents of the target cells, a cytotoxicity mechanism based on the disturbance of a fundamentally vital function of the cell, namely its capacity for protein synthesis, and a very low level of non-specific toxicity, compared with the level of specific toxicity, insofar as the A chain does not by itself possess the property of penetrating into the cells without being bonded to another suitable molecule which permits fixation to the cell membranes. In the case of ricin, this suitable molecule is the B chain, and, in the case of the invention, it is a specific immunoglobulin which is capable of recognising a specific receptor at the surface of the target cells and of creating, with this receptor, an association which possesses a high association constant.

An attempt to produce conjugates between immunoglobulins and constituent peptide chains of ricin has been reported [Annals of the New York Academy of Sciences 277, 690 (1976)]. However, the specificity obtained in vitro in this experiment is extremely low for various reasons, namely:

the A chain of ricin was not isolated from the B chain before conjugation with the antibody, the antibodies used were not pure and contained large amounts of non-antibody proteins and of antibodies other than those which are specifically directed against the target antigen, and the coupling of the toxin with the antibody was carried out using glutaraldehyde, this being a product which is capable of causing the denaturation of the antibody or of the toxin by the formation of bridges, in a non-specific manner, inside a peptide chain or between the various peptide chains, and this amounts to random polymerisation.

The present invention makes it possible to overcome all these difficulties and to obtain conjugates which possess a pronounced specificity for the target cells and can be used for the treatment of cancer.

ISOLATION AND PURIFICATION OF RICIN AND OF ITS A CHAIN

The seed of Ricinus communis contains the toxic lectin known by the name ricin. It also contains another, less toxic, lectin which is denoted by the name agglutinin because of its agglutinating properties with respect to cells and, in particular, with respect to red blood cells. This agglutinin consists of two sub-units, each of which results, in the same way as ricin, from the association of two glycoprotein chains by means of a disulphide bridge.

Finally, the seed of Ricinus communis contains other proteins of diverse natures and also a large amount of lipids which are the constituents of castor oil.

The extraction of ricin starts by grinding the seeds of Ricinus communis to produce a paste from which the oil must be removed by means of a solvent for the lipids, for example by repeated extractions with ethyl ether. After drying, the powder obtained is extracted cold by stirring with a solution of sodium chloride in a slightly acid medium, preferably at a temperature which does not exceed 4° C. After separating off the sediments, the extract is dialysed for a long time, firstly against water and then against a buffer of low ionic strength (TRIS-HCl, 10 mM, pH=7.7). A slight precipitation occurs during dialysis; the precipitate is separated off by filtration or centrifugation.

The extract thus obtained contains all the soluble proteins of the Ricinus communis seed, namely ricin, agglutinin and various other proteins. This solution can be frozen at −20° C., at which temperature it keeps for several weeks.

The preparation of pure ricin from the crude extract has already been described in the literature. In general, it involves chromatographic techniques, namely ion exchange chromatography, chromatography on a molecular sieve or also affinity chromatography. Most frequently, these various methods are combined with one another, giving rise to long and difficult techniques which cannot easily be applied to give large amounts of ricin. According to the invention, it is possible to obtain pure ricin by means of a single affinity chromatography operation which makes it possible to separate the ricin successively from the foreign proteins and then from the agglutinin. To do this, the crude extract is deposited on a column of Sepharose 4B (an agar gel in the form of spherical particles, at a concentration of 4%, marketed by the Pharmacia Company) and then eluted in a sequential manner. Using a TRIS-HCl buffer, 50 mM, pH=7.7, the proteins in the seed which are not lectins are eluted, and then, using a galactose solution having a concentration of between 0.28 and 0.56 mM, the pure ricin is obtained. Finally, using a 0.1 M galactose solution, the agglutinin is obtained. Total separation of the constituents from one another is achieved in a single chromatography operation if the volume of Sepharose 4B used in such that the total amount of protein introduced into the column does not exceed the capacity of the latter.

After this step, concentration by ultrafiltration makes it possible easily to obtain a solution of pure ricin, containing from 5 to 10 mg/ml of product in a buffer of low ionic strength. The solution also contains a small amount of galactose (about 0.4 millimol/liter). Frozen at −20° C., this solution can keep for several weeks.

The two constituent chains of ricin can be separated after selective splittering of the single disulphide bridge which joins them. This splittering is carried out by means of a reducing agent, such as 2-mercaptoethanol or dithiothreitol, of which the concentration in the reaction medium must be at least 2%.

The separation of the two chains, by methods using ion exchange on various types of support, has already been described, which methods are essentially based on the differences in the isoelectric points of the two chains. According to the invention, a process for separating the two chains A and B of ricin has been developed, which utilises not only the difference in the isoelectric points of the two chains, but also their different affinities towards the polysaccharide chromatographic supports containing galactose derivatives. The use of such supports also exhibits the advantage that they retain any possible traces of undivided ricin which could remain in the mixture.

In practice, the reducing agent (for example 2-mercaptoethanol) is added, at ambient temperature, to the solution of ricin, obtained above, in the buffer of low ionic strength, until a concentration of 2.5% volume/volume is reached, and the solution is then deposited on a column, consisting of DEAE CL Sepharose 6B (a gel marketed by the Pharmacia Company and used for ion exchange chromatography; it is prepared from Sepharose, or agar gel, by crosslinking with 2,3-dibromopropanol and removing the sulphate groups by alkaline hydrolysis and then introducing diethylaminoethyl groups; concentration 6% in the gel), in the same buffer containing the reducing agent. The two chains bind the column by means of bonds which are ionic with respect to the DEAE groups, and the B chain also becomes fixed to the Sepharose matrix by virtue of affinity.

The A chain is eluted by increasing the ionic strength and the pH, still in the presence of the reducing agent so as to prevent any recombination of the two chains with one another (elution buffer: 0.1 M TRIS-HCl, pH=8.4, which is 0.1 M in respect of NaCl and contains 2.5% of 2-mercaptoethanol). Under these conditions, the B chain remains totally fixed. It can be eluted by the same buffer which is 0.2 M in respect of sodium chloride and 0.1 M in respect of galactose.

A variant of the process for separating the A and B chains consists in using, for chromatography, a support on which the ion exchange and molecular sieving phenomena occur simultaneously. Thus, using QAE Sephadex A.50 (a strong basic ion exchanger obtained by fixing quaternary ammonium groups to Sephadex, or dextran gel, by means of ether bonds, and marketed by the Pharmacia Company), the pure A chain can be eluted with the TRIS-HCl buffer, 100 mM, pH=8.4, containing 0.5% of 2-mercaptoethanol, whilst the B chain is eluted with the same buffer which, in addition, is 75 mM in respect of sodium chloride.

In either case, the choice of the chromatographic support is very important and various other supports tested have not made it possible to achieve a good separation of the A chain.

The A chain obtained by one or other of these processes was shown to be pure with respect to the various analytical criteria and does not require further purification. However, in order to effect its subsequent coupling with antibodies, it is necessary to have available fairly concentrated solutions which are free, in particular, from the reducing agent. In order to do this, the solution of A chain in TRIS, obtained above, is dialysed against a 10 mM phosphate buffer, pH=6.5, and this simultaneously removes the TRIS, the sodium chloride, the 2-mercaptoethanol and the traces of galactose.

The solution thus obtained is deposited on a column of carboxymethylcellulose, and the A chain is then eluted by simultaneously increasing the concentration and the pH of the buffer from 10 mM, pH=6.5, to 125 mM, pH=7.0, the buffer being 1 mM in respect of EDTA. A fairly concentrated solution (about 5 mg/ml), which is ready for the coupling reactions, is thus obtained.

The diluted solution thus obtained can also be concentrated and purified by subjecting said solution to a concentration step on C. M. Sepharose ® support, combining the ion exchange and affinity effects, and a solution presenting simultaneously a high concentration and a high level of pureness, can be obtained. Furthermore, such a solution causes the A chain to deposit by cooling in a crystallised form.

The A chain thus prepared (in the state of concentrated solution or in the state of crystals) is free of non-specific toxicity towards cellular systems or animal bodies, and therefore can be used for producing conjugates, the specificity of which is strictly provided by the antibody.

PREPARATION OF PURE ANTIBODIES

According to the invention, the preparation of the antibodies is carried out so as to give pure antibodies which are free from molecules without antibody activity, in order to impart the most complete specificity of action to the conjugates prepared subsequently, this being a characteristic which is not observed in the preparations described in the literature.

Immunisation is carried out repetitively for several months, in accordance with a conventional process, in order to achieve a hyper-immunisation of the animals. Several liters of immunoserum are thus collected and this can be stored at −20° C. before subjecting it to the purification operations.

The purification is effected by immunoadsorption using a Sepharose 4B gel, activated by cyanogen bromide, to which an antigen corresponding to the specific antibody to be purified has been fixed. After separating off the liquid phase, intense washing makes it possible to remove all the proteins which are not fixed to the gel, and the antibodies fixed to the gel are then liberated with a suitable eluent. This method can be applied to various antibodies of different specificities. According to the invention, the population of antibodies in the serum can thus be fractionated so as to select the antibodies which have the highest affinity for the antigen. With an excess of antibodies, relative to the amount of antigen fixed to the gel, the gel preferentially retains the antibodies which have the highest affinity.

In practice, the process is carried out with an excess of antibodies which is such that only a fraction of the antibodies in the immune serum is fixed to the column, whilst the remainder are removed by washing. Under these conditions, the average affinity of the antibodies which are removed by washing is lower than that of the antibodies which are fixed to the column and subsequently eluted. A population of antibodies is thus obtained which has a more homogeneous affinity than the population present in the starting immune serum.

If it is desired to work with large amounts of antibodies, which requires columns of large dimensions, the amount of immune serum to be used on a given gel, containing the antigen, is determined beforehand by carrying out a series of microimmunoadsorptions with increasing amounts of antiserum. Determination of the antibodies in the eliminated liquid phase by the radioimmunological method makes it possible to determine the ratio of antigen/antibody which allows the undesirable fraction of the antibody initially introduced to escape into this phase.

PREPARATION OF THE A CHAIN OF RICIN/ANTIBODY CONJUGATES

The object of this part of the invention is to associate, by means of a covalent bond of the disulphide type, on the one hand, an immunoglobulin which is specific for a given antigen, or any fragment of this molecule which possesses the capacity of specific recognition with respect to the antigen, with, on the other hand, the A chain of ricin. The choice of a disulphide bond between the A chain and the immunoglobulin is based on the following arguments:

this type of bond is the type which exists in the natural ricin molecule, and it can be expected to be particularly suitable for presenting the A chain in a conformation which facilitates its penetration into the cell, whilst at best retaining its fundamental biological property of inhibiting protein synthesis, this type of bond is biochemically labile, which provides the A chain, coupled in this way, with the possibility of being liberated, from its carrier protein, in the contents of the cell, the A chain of ricin possesses a single cysteine residue in its structure and hence only one SH group capable of creating a disulphide bond. Consequently, the conjugates formed by involving this SH group in a disulphide bridge will be chemically well defined and will in no way modify the structure of the A chain, thus ensuring the integral retention of its biological activity, and there are efficient methods which make it possible to produce such a disulphide bond under conditions which are sufficiently mild to ensure the integrity of the biological properties of the protein constituents of the conjugates formed.

In order to produce such conjugates, the proteins to be coupled must each carry at least one sulphur atom which is naturally capable, or is artificially rendered capable, of creating the desired disulphide bond, whether these sulphur atoms already exist in the proteins or have been chemically introduced into these proteins. As indicated above, the A chain of ricin naturally possesses only one sulphur atom permitting the desired coupling. This is the sulphur atom in the thiol group of the single cysteine residue incorporated in the A chain. As regards the immunoglobulin or its fragments, several cases must be considered:

(1) In the case of an entire immunoglobulin, neither a free thiol group nor other sulphur atoms capable of being used for the coupling exist naturally in these proteins. It will therefore be necessary, in this case, to introduce one or more sulphur atoms into the immunoglobulin molecule artificially so that:

the biological properties of the immunoglobulin are not profoundly impaired, and this sulphur atom, or these sulphur atoms, can subsequently be involved in the disulphide bond to be established with one or more molecules of the A chain of ricin.

(2) In the case of a Fab fragment, the situation is absolutely identical to that described above.

(3) If a fragment of the Fab' type is employed, it is possible to use the sulphur atom present in the free thiol group to carry out the coupling to the A chain. However, it is also possible to use the artificial introduction of one or more sulphur atoms; in this case, it is necessary to block the free thiol group in a stable manner beforehand, for example by alkylation.

(4) Finally, if it is desired to couple a F(ab')$_2$ fragment of immunoglobulin, it is necessary, as in the case of the whole immunoglobulin, to introduce one or more sulphur-containing groups into F(ab')$_2$ artificially.

In all the cases in which one or more sulphur-containing radicals are introduced into the immunoglobulin or its fragments, it is necessary to avoid any substitution in the site for recognition of the antigen or in its immediate environment, which substitution could disturb the recognition properties of the antibody. In order to exclude this risk, the site for recognition of the antigen can be blocked temporarily, during the substitution reaction, by treating the antibody beforehand with the specific antigen, or with another antigen which possesses an adequate cross-reaction, or with a suitable hapten.

The operation for temporary protection can be carried out:

either in the liquid phase, if the antibody-antigen (or hapten) complex is soluble in the reaction medium, or in the heterogeneous phase, if this complex is spontaneously insoluble or also if it has been deliberately rendered insoluble by means of a suitable procedure, in particular by fixing the antigen (or hapten) to an insoluble support so that the modified support thus obtained possesses an adequate affinity for the antibody.

After the substitution step, it will be necessary to unblock the site for recognition of the antigen, on the antibody, by means of a suitable procedure for removing the antigen, in order to regenerate the capacity of the antibody for specific recognition.

To produce the disulphide bridge between the two proteins, it is not possible to bring the two constituents of the conjugate, each carrying a SH group, into contact with one another and to carry out an oxidation. In fact, under these conditions, the coupling reaction is an equilibrium reaction which is very difficult to drive to completion. Furthermore, the desired reaction is accompanied by the formation of polymers of each of the two constituents, which would result in a very low yield of the desired product and the presence of impurities which are very difficult to remove.

According to the invention, the conjugate is prepared by bringing one of the proteins, carrying its free SH group, into contact with the other protein, in which the SH group is activated by conversion into a mixed disulphide with a suitable sulphur-containing organic radical. The preparation of the conjugate can be represented by the equation:

$$P_1\text{-SH}+P_2\text{-S-S-X}\rightarrow P_1\text{-S-S-}P_2+\text{XSH}$$

in which $P_1$ and $P_2$ represent the two proteins to be coupled and X denotes the activator radical. It is immediately apparent from this equation that, in each case, the coupling reaction can be carried out in accordance with two variants, depending on whether $P_1$ represents the immunoglobulin or its fragment and $P_2$ represents the A chain of ricin, or vice versa.

Case in which $P_1$ represents the antibody or a fragment and $P_2$ represents the A chain of ricin To activate the free SH in the A chain of ricin, the solution of A chain, prepared as indicated above, is used, and it is subjected to an exchange reaction:

$$\text{ASH}+\text{XSSX}\rightleftarrows\text{A-S-S-X}+\text{XSH} \quad (1)$$

in which ASH represents the A chain of ricin and X represents the activator radical.

In particular, X can denote a pyrid-2- or -4-yl group which is optionally substituted by one or more alkyl or halogen radicals or carboxylic acid groups, or X can also represent a phenyl nucleus which is optionally substituted by one or more nitro or carboxylic acid groups. Reaction (1) is an equilibrium reaction but the equilibrium can easily be displaced towards the right by using a large molar excess of the reagent XSSX, which is generally inexpensive and readily accessible. It is possible to monitor the course of reaction (1) by ultraviolet or visible spectrophotometry because the compound XSH which is formed shows an intense absorption in this region. When the reaction has reached the desired degree of completion, the excess of the reagent X-S-S-X, and also the reaction product X-SH, are removed by dialysis or filtration on a molecular sieve in gel form. Finally, a pure solution of the compound A-S-S-X in the chosen buffer is obtained. If necessary, this solution can be kept for several weeks after freezing.

The immunoglobulin substituted by a SH group is also prepared. To do this, the solution of immunoglobulin obtained above is used either as such or after blocking its site for the recognition of the antigen, with the corresponding hapten, followed by removal of the excess hapten. By reacting S-acetylmercaptosuccinic anhydride with this protein, it is possible to fix one or more S-acetylmercaptosuccinyl groups, per molecule of protein, by means of its free amino groups, and then to liberate the thiol groups by the action of hydroxylamine, as has been described [Archives of Biochemistry and Biophysics 119, 41-49 (1967)]. Dialysis makes it possible to remove the excess reagents and also the reaction products of low molecular weight.

All these operations are carried out in a phosphate buffer at pH=7.0 and at temperatures which do not exceed ambient temperature. The hapten which may have been used as a temporary blocking agent is removed from the solution finally obtained. If it proves necessary, this solution can be concentrated, for example by ultrafiltration. The coupling between the two reagents thus prepared is effected by simple contact in aqueous solution, at ambient temperature, for a time varying from a few hours to one day, in accordance with the equation:

(4)

The course of the reaction is followed by spectrophotometric determination of the compound XSH formed. The latter is removed by dialysis and a solution of the expected conjugate is obtained which must be further purified. In fact, it is essential, in particular, to remove the molecules of A-S-S-X which have not reacted and which, if they were present in the conjugate, could give rise to a non-selective toxicity.

The purification can be effected by various known methods such as fractional precipitation with the aid of water-miscible organic solvents or of salts, gel permeation chromatography, or also affinity chromatography on a column formed by an insoluble support on which the antigen (or the hepten) is fixed, against which antigen the antibody employed in the preparation of the conjugate is directed.

These purification methods can be applied directly to the dialysed solution originating from the coupling step. However, better results are obtained, and, in particular, the subsequent formation of polymers of the conjugate is avoided, by the prior blocking of the SH groups which remain free, with a reagent such as N-ethylmaleimide.

Case in which $P_1$ represents the A chain of ricin and $P_2$ represents the antibody In this case, the products required for the coupling are the A chain of ricin and the immunoglobulin (or its fragment), which is substituted by a group carrying one or more activated sulphur atoms. The A chain of ricin is used as obtained by the purification procedure described. The immunoglobulin substituted by an activated sulphur atom is prepared from the immunoglobulin itself by substitution with the aid of a reagent which itself carries an activated sulphur atom, in accordance with the equation:

$$\text{Prot}+\text{Y-R-S-S-X}\rightarrow\text{Prot-R-SS-X}$$

in which Prot denotes the immunoglobulin, Y represents a group permitting the covalent fixation of the reagent to the protein, R denotes a group which can simultaneously carry the substituents Y and -S-SX, and X denotes the activator radical.

A reaction of this type has already been used for coupling two proteins (identical or different) by means of a disulphide bridge, but the application of this principle to the coupling of an immunoglobulin with the A chain of ricin is new.

The functional group Y is a group which is capable of bonding in a covalent manner with any one of the groups carried by the side chains of the constituent aminoacids of the protein to be substituted. Amongst these latter groups, the terminal amino groups of lysyl radicals, which are present in the protein, are particularly indicated. In this case, Y can represent, in particular:

a carboxylic acid group which can bond to the amino groups of the protein in the presence of a coupling agent such as a carbodiimide and, in particular, a water-soluble derivative such as 1-ethyl-3-(3-diethylaminopropyl)-carbodiimide, a carboxylic acid chloride which is capable of reacting directly with the amino groups in order to acylate them, a so-called "activated" ester, such as an ortho- or para-, nitro- or dinitro-phenyl ester or also a N-hydroxysuccinimide ester, which reacts directly with the amino groups in order to acylate them, an internal anhydride of a dicarboxylic acid, such as, for example, succinic anhydride, which reacts spontaneously with the amino groups in order to create amide bonds, or an iminoester group in which $R_1$ is an alkyl group which reacts with the amino groups of the protein in accordance with the equation:

X denotes a functional group which is capable of reacting with a free thiol radical.

In particular, X can denote a pyrid-2-yl or pyrid-4-yl group which is optionally substituted by one or more alkyl, halogen or carboxylic acid radicals. X can also denote a phenyl group which is preferably substituted by one or more nitro or carboxylic acid groups. X can also represent an alkoxycarbonyl group such as the methoxycarbonyl group.

The radical R denotes any radical which is capable of simultaneously carrying the substituents Y and S-S-X. The radical chosen must not contain groups which are capable of interfering, in the course of the subsequent reactions, with the reagents used and the products synthesised. In particular, the group R can be a group $-(CH_2)_n$, in which n is between 2 and 10, or also a group in which $R_4$ denotes hydrogen or an alkyl group having from 1 to 8 carbon atoms, and $R_3$ denotes a substituent which is inert towards the reagents subsequently used, such as an amide group in which $R_5$ denotes a linear or branched alkyl group having from 1 to 5 carbon atoms, in particular the tert.-butyl group.

The reaction of the compound Y-R-S-S-X with the immunoglobulin is carried out in the homogeneous liquid phase, most frequently in water or a buffer solution. When required by the solubility of the reagents, it is possible to add, to the reaction medium, up to 20% by volume of a water-miscible organic solvent such as an alcohol, in particular tertiary butanol.

The reaction is carried out at ambient temperature for a time which varies from a few hours to 24 hours. Thereafter, dialysis makes it possible to remove the products of low molecular weight and, in particular, the excess reagents. This process makes it possible to introduce a number of substituent groups of between 1 and 5 per molecule of protein.

Using such compounds, the coupling with the A chain of ricin is carried out by bringing the two proteins into contact with one another in aqueous solution, at a temperature which does not exceed 30° C., for a time which varies from a few hours to one day. The reaction takes place in accordance with the equation:

$$\text{Prot-R—S—S—X} + \text{ASH} \longrightarrow \text{Prot-R—S—S—A} + \text{XSH}$$

in which Prot-R-S-S-X represents the substituted immunoglobulin (or its fragment), activated on the sulphur atom, and ASH represents the A chain of ricin. The solution obtained is dialysed in order to remove the products of low molecular weight, and the conjugate can then be purified by various known methods, as indicated in the first process for the preparation of the conjugates.

The characteristics of the present invention will be understood more clearly in the light of the following examples which illustrate the invention without limiting the scope thereof.

In the examples which follow, TPE will denote the 0.125 M phosphate buffer, pH=7.0, which is 1 mM in respect of the disodium salt of ethylenediaminetetraacetic acid.

EXAMPLE 1

Preparation of the Ricin

(a) Extraction 1 kg of whole unshelled seeds of Rricinus communis is ground in a knife-type chopper to give a paste, and this paste is triturated carefully with 2 liters of ethyl ether cooled to 4° C. After removal of the ether, the lipid-removing operation is repeated a further two times with 2 liters of ether each time. After the last removal of ether, the residue is dried in air and provides 400 g of fat-free powder. This powder is suspended in 3,400 ml of a 0.14 M solution of sodium chloride, cooled to 4° C., and the pH of the suspension is brought to a value of 4 by adding acetic acid. The suspension, cooled in an ice bath, is subjected to a homogenisation operation involving rapid agitation in the bowl of a knife-type mill for 30 seconds, followed by a 30 minute rest period with cooling in an ice bath. This homogenisation/rest cycle is repeated 8 times.

After completion of the extraction, the suspension is centrifuged and provides about 3,400 ml of a clear solution. The latter is transferred into a dialysis tube having a flat width of 10 cm, and is dialysed firstly against distilled water (which is continuously renewed) for 48 hours and then for 24 hours against the TRIS-HCl buffer, 10 mM, pH=7.7, which is continuously renewed at a rate of 1 liter/hour. During the dialysis, a precipitate forms which is removed by filtration on a glass frit. 3,400 ml of a crude solution containing 12 mg/ml of proteins are thus collected. This solution can be stored at −20° C.

(b) Purification

A column having an internal diameter of 100 mm is filled with 5 liters of Sepharose 4B (Pharmacia) and equilibrated with the TRIS-HCl buffer, 10 mM, pH=7.7, cooled to 4° C.

1,700 ml, that is to say half of the crude solution obtained above, is deposited at the top of this column at a rate of 300 ml/hour. The column is then washed with 3 liters of TRIS-HCl buffer, 10 mM, pH=7.7, whilst maintaining the same flow rate, and the filtrate, containing the proteins which have not been fixed to the column by virtue of affinity, is removed.

Elution is then carried out, still at the same flow rate, with 4 liters of the same buffer containing 0.050 g (0.28 millimol) of galactose per liter, and this fraction is collected. Elution is then carried out, still with a flow rate of 300 ml/hour, with 4 liters of the same buffer containing 0.100 g (0.56 millimol) of galactose per liter. This fraction is combined with the preceding fraction to provide 8 liters of a solution containing about 300 mcg of ricin per ml.

In order to be able to re-use the column for a subsequent operation, the latter is eluted with 1 liter of the TRIS-HCl buffer, pH=7.7, which contains 18 g (0.1 mol) of galactose per liter, to provide a fraction which essentially contains agglutinin and is removed. After washing with a further 1 liter of the same buffer and then with several liters of the pure TRIS-HCl buffer, pH=7.7, the column is again ready for use.

An identical operation is carried out on the other half of the crude solution obtained in paragraph a. The eluted fraction is combined with the preceding fraction to produce 16 liters of a solution of ricin in the TRIS-HCl buffer, 10 mM, pH=7.7, which contains an average of 0.075 g of galactose per liter.

This solution is concentrated on an ultrafiltration membrane, the porosity of which permits the passage of globular molecules of molecular weight <30,000, in a cell of diameter 150 mm. 762 ml of a solution of ricin in the original buffer, containing 6.7 mg/ml, is finally obtained. This solution can be stored at −20° C.

The ricin thus obtained possesses the following characteristics:

Molecular weight: 66,000±5,000, determined by electrophoresis in the presence of sodium dodecyl-sulphate in accordance with Journal of Biological Chemistry 244, 4,406-4,412 (1969).

Isoelectric point: 7.1, determined by free electrophoresis [Laboratory techniques in biochemistry and molecular biology, Volume 5, part II, page 501, Publishers: T. S. WORK and E. WORK (North Holland)].

All the conventional analytic methods applied to the ricin thus obtained make it possible to allow the conclusion that the product is pure.

EXAMPLE 2

Preparation of the A Chain of Ricin 3.75 ml of 2-mercaptoethanol are added to 150 ml of the solution of ricin, obtained in Example 1 and containing about 1 g of ricin, and the solution is left for 2 hours at 20° C.

This solution is then deposited on the top of a column of internal diameter 50 mm, filled with 1,800 ml of DEAE CL Sepharose 6B (Pharmacia) and equilibrated with the TRIS-HCl buffer, 0.1 M, pH=8.4, which contains 2.5% (volume/volume) of 2-mercaptoethanol.

The column is washed with 300 ml of the TRIS-HCl buffer 0.1 M, pH=8.4, which is 0.1 M in respect of sodium chloride and contains 2.5% (volume/volume) of 2-mercaptoethanol. A single fraction is collected after the beginning of the loading operation (about 450 ml) and contains the A chain, identified by electrophoresis, at a concentration of about 0.89 mg/ml.

This fraction is carefully dialysed, in a dialysis tube having a flat width of 10 mm, against 10 mM phosphate buffer, pH 6.5. This solution is deposited on a column of internal diameter 25 mm, which contains 300 ml of carboxymethylcellulose CM 52, marketed by Whatman, and is equilibrated with the 10 mM phosphate buffer, pH=6.5. Under these conditions of pH and ionic strength, the A chain becomes fixed and it is then eluted with TPE. 67 ml of a solution of A chain, containing 5.72 mg/ml, are thus collected.

The A chain possesses the following characteristic, determined in the same ways as those mentioned in the case of ricin (Example 1):

Molecular weight: 30,000±3,000.

isoelectric point: 7.5.

Furthermore, in accordance with the DTNB technique [Methods in Enzymology 25, 457 (1972) (Academic Press)], 0.96 equivalent of SH was determined per mol of A chain, the latter having an estimated molecular weight of 30,000. The column of DEAE CL Sepharose 6B used for the separation can be regenerated, for re-use, by washing with the TRIS-HCl buffer, 0.1 M, pH=8.4, which is 0.1 M in respect of sodium chloride and 0.1 M in respect of galactose and elutes the B chain fixed to the column. The column must then be re-equilibrated with the TRIS-HCl buffer, 0.1 M, pH=8.4, which contains 2.5% of 2-mercaptoethanol, for the purpose of a further preparation of the A chain.

Concentration of the A Chain of Ricin

The A chain obtained in diluted solution is deposited on a chromatography column of internal diameter 16 mm containing 10 ml of Sepharose ® carboxymethyl equilibrated with the same buffer. Under these conditions, the A chain becomes fixed; it is then eluted with the TPE buffer. The recovery is quantitative.

A deposit of 150 mg of A chain permits fractions to be eluted at the average concentration of 10 mg/ml of A chain, representing a total of 90% of the quantity deposited on the column.

The resulting concentrated solution is very pure.

Obtaining A Chain Crystals

A solution of A chain with a concentration equal to 10 mg/ml is left at 4° C. After a few days, crystals develop, whose analysis, after re-dissolution, shows that they possess the same physico-chemical (molecular weight, isoelectric point) and biological properties (inhibition of the protein synthesis) as the A chain, from which they are issued.

EXAMPLE 3

Preparation of the A Chain of Ricin 1.75 ml of 2-mercaptoethanol are added to 70 ml of a solution of ricin, obtained in accordance with the technique of Example 1 and containing 4 mg/ml of ricin, and the solution is left for 2 hours at 20° C.

This solution is deposited on a column containing 800 ml of QAE Sephadex A50 (Pharmacia) and equilibrated with the TRIS-HCl buffer, 100 mM, pH=8.4, which contains 0.5% (volume/volume) of 2-mercaptoethanol. Elution is carried out with the same buffer.

From the time of deposition, a 170 ml fraction, containing 0.9 mg/ml of A chain, is collected and then treated as indicated in Example 2, starting from the dialysis operation. The A chain thus obtained possesses the same characteristics as those obtained in Example 2. In order to regenerate the column, the fixed B chain can be eluted with the TRIS-HCl buffer, 100 mM, pH=8.4, which is 0.15 M in respect of added sodium chloride, and the column can then be washed with the TRIS-HCl buffer, 10 mM, pH=7.7.

EXAMPLE 4

Preparation of Pure Anti-DNP Antibodies

The term anti-DNP antibodies denotes antibodies which are specifically directed against the 2,4-dinitrophenyl radical.

(a) Immunisation of the Animals

The desired immunogen is produced by reacting 2,4-dinitrobenzenesulphonate with bovine γ-globulin in accordance with a conventional technique, leading to the fixation of 52 2,4-dinitrophenyl groups per molecule of protein ($DNP_{52}$-BGG). By immunisation with this product, a fraction of the antibodies formed will be specifically directed against the hapten 2,4-dinitrophenyl.

Three male goats are each immunised by injection with 5 mg of $DNP_{52}$-BGG in an emulsion obtained from 2 volumes of physiological salt solution, buffered to pH=7.4, per volume of Freund's complete adjuvant. The first immunisation is followed by 7 booster injections spread out over one year. During the same period, 12 1 liter samples of blood are taken from the veins of each animal. The serum is prepared and kept at −20° C. Prior to the purification step, 17 samples are combined and in the pool thus obtained, the complement is destroyed by heating. Centrifugation is then carried out for 30 minutes at 20,000×g in order to remove the denaturated proteins and the aggregates, and, finally, paper filtration is carried out in order to retain the suspended fats. The serum thus prepared is ready for the purification step.

(b) Purification

The purpose of this step is the specific adsorption of the anti-DNP antibodies from the serum onto a protein carrying the hapten 2,4-dinitrophenyl and fixed to a solid support. The free or non-specifically bound substances are subsequently removed and the pure antibodies are then eluted.

Preparation of the Immunoadsorption Support

The immunoadsorption gel is formed by coupling 1,630 mg of human serum albumin, carrying 35 dinitrophenyl groups ($DNP_{35}$-HSA), and 100 g (dry weight) of Sepharose 4B in accordance with the conventional technique. Spectrophotometric determination at 280 nm and 360 nm of the wash waters after coupling makes it possible to establish a 95% efficiency for the fixation of $DNP_{35}$-HSA. Two washing cycles are carried out: firstly at pH=3.0 (0.8 M glycine hydrochloride buffer which is 1 M in respect of sodium chloride) and then at pH=10.0 (0.1 M borate buffer which is 1 M in respect of sodium chloride). The gel is then equilibrated in the working buffer, the latter being a 0.1 M phosphate buffer, pH=7.0, which contains 0.01% (weight/volume) of sodium azide.

Adsorption of the Antibodies

Before carrying out the adsorption onto the gel prepared above, it is necessary to determine the volume ratio of serum/gel to be used, so that only those anti-DNP antibodies possessing the strongest affinity are fixed to the support. In order to achieve this result, it was decided to fix only 50% of the overall antibody activity of the serum to the column, leaving the other 50% in the supernatant liquid.

For a given serum, the determination of the amount of gel to be used is carried out by working on small amounts under analytical conditions. 125 μl aliquots of the immunoadsorbent gel are brought into contact with volumes of serum of 0.5 ml to 8 ml, increasing in a geometric progression with a factor of 2. After incubation, the supernatant is determined with respect to its anti-DNP antibody activity by a conventional radioimmunological method [Handbook of Experimental Immunology, Volume 1, chapter 15, pages 1-18, Publisher D. M. WEIR, second Edition, 1973], using ε-N-(2,4-dinitrophenyl)-L-lysine tritiated on the phenyl nucleus in the 3- and 5-positions.

Thus, for each experiment, it is possible to express the antibody activity which has remained in the supernatant by a percentage (A) of the activity of the starting immune serum before treatment with the gel, and to plot the corresponding curve A (%) versus f (volume ratio of serum/gel). This curve shows the amount of serum required, with 125 μl of gel, for 50% of the antibody activity to remain in the supernatant liquid. In the experiment described, this amount is 4 ml or also 32 ml of serum per ml of immunoadsorption gel.

With this ratio determined, 6,150 ml of immune serum are stirred, in a 10 liter container, with 193 ml of immunoadsorbent gel for 1 hour at ambient temperature and then overnight at 4° C.

After centrifugation (1,000×g, 10 mins), the gel is separated off and the solid deposit is re-suspended in 1 volume of supernatant liquid. This suspension is transferred onto a chromatography column (diameter 26 mm, length 400 mm) which is equipped with a cooling jacket at 4° C., a device for recording the optical densities at 280 nm and a fraction collector. The column is then washed with 8 liters of 0.1 M phosphate buffer, pH=7.0, which contains 0.01% of sodium azide. Washing is carried out for 40 hours at 4° C. and then for 24 hours at ambient temperature. When the washing is complete, the optical density at 280 nm is extremely low (OD<0.04).

Elution of the Antibodies

The elution of the anti-DNP antibodies fixed to the column is effected with a large excess of a solution of the hapten 2,4-dinitrophenol.

A 0.2 M solution of 2,4-dinitrophenol is used in the same phosphate buffer used above, the acidity of which has been neutralised to pH=7.0 by adding sodium hydroxide. The solution thus obtained must be kept in the absence of light. For the elution, 2.8 liters of this solution are used and are passed through the column at a rate of 125 ml/hour. In order to remove the 2,4-dinitrophenol from the eluted solution, the latter is immediately passed through a second column which contains 300 ml of Dowex 1×10 resin (an ion exchange resin consisting of a styrene/divinylbenzene polymer carrying quaternary ammonium radicals) and is equilibrated in the phosphate buffer used for washing.

The antibodies are eluted in a single peak of proteins, followed by a tail. On the one hand, the resulting fractions of optical density ≧0.9 (fraction $B_1$, 700 ml), and, on the other hand, the other fractions (fraction $B_2$, 2,000 ml), are combined. The concentration of protein in each of the fractions is determined in accordance with Journal of Immunological Methods 15, 101-119 (1977).

Fraction $B_1$ contains 15.4 g, that is to say 22 g/liter, of antibodies and fraction $B_2$ contains about 1 g, that is to say 0.5 g/liter, of antibodies. The fractions are kept at −20° C. in the 0.1 M phosphate buffer, pH=7.0, used for washing, which contains 0.01% of sodium azide.

The various physicochemical methods used, in particular agar gel thin layer electrophoresis, immunoelectrophoresis and passage through a column of Sephadex G 200 (a dextran gel in the form of beads, obtained by crosslinking dextran fractions with epichlorohydrin and used for gel filtration), allow the conclusion that the antibodies obtained are pure and, in particular, that detectable amounts of albumin (less than 1/500 of the antibodies) and of immunoglobulins M are absent in the preparations obtained.

The immunological activity of the purified antibodies was determined by the method of NAHM [Journal of Immunology 119, 1,301 (1977)] and compared with that of the starting immun serum and that of the antibodies present in the supernatant from immunoadsorption (fraction $A_1$).

| | Mean association constant | Affinity dispersion index |
|---|---|---|
| Immunoserum | $2.0 \cdot 10^7 mol^{-1}$ | 0.50 |
| Fraction $A_1$ | $5 \cdot 10^5 mol^{-1}$ | 0.22 |
| Fraction $B_1$ | $2.5 \cdot 10^7 mol^{-1}$ | 0.75 |

These results indicate that the purified antibodies (fraction $B_1$) possess:

a higher mean affinity than the starting immune serum and, of course, than fraction $A_1$, and a greater homogeneity of affinity than the immune serum.

EXAMPLE 5

Preparation of the Conjugate Obtained from Anti-DNP Antibodies Containing Mercaptosuccinyl Groups and from the Activated A Chain of Ricin (a) Preparation of the Activated A Chain of Ricin 15 ml of a solution of A chain in the phosphate buffer (Example 2), containing 1.4 mg/ml of A chain, are mixed with 8 ml of a 1.425 mM solution of 2,2'-bipyridyldisulphide in the same buffer. The solution is left to stand at ambient temperature and in the absence of light for 1 hour 30 minutes. A solution of A chain activated on the thiol group, containing 0.9 mg of protein per ml, is thus obtained. After reaction, spectrophotometric determination at 343 nm indicates that the product formed contains 0.9 activated group 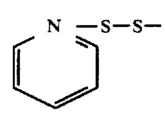 per molecule of A chain. The solution is purified by continuous dialysis for 18 hours, at a temperature of 5° C., against TPE. The pure solution is kept at −20° C.

(b) Preparation of the Anti-DNP Antibody Containing Mercaptosuccinyl Groups 0.37 ml of an aqueous solution of 2,4-dinitrophenol, containing 0.57 mg/ml, is added to 3.3 ml of a solution of anti-DNP antibodies (Example 4), containing 25.8 mg/ml of pure antibodies, and the mixture is stirred for 10 minutes at ambient temperature. This solution is added quantitatively to 3.06 mg of S-acetylmercaptosuccinic anhydride [Archives of Biochemistry and Biophysics 96, 605–612 (1962)] and the mixture is stirred for 2 hours at ambient temperature.

0.47 ml of a 0.1 M aqueous solution of hydroxylamine, pH=8.0, is added to this solution, and the mixture is left for 1 hour 30 minutes at ambient temperature. The preparation of dialysed against 4 times 3 liters of TPE for 89 hours at 5° C. and the dialysed solution is then centrifuged at 27,000×g for 10 mins at 4° C. The supernatant is passed through a column of Dowex 1×8 resin of 200 to 400 mesh particle size, in the phosphate form, in order to remove the 2,4-dinitrophenol which is fixed to the site for recognition of the antigen.

Elution is carried out with TPE at ambient temperature and the solution is then concentrated by ultrafiltration. Finally, 4.55 ml of a solution containing 17.0 mg/ml of antibodies containing mercaptosuccinyl groups are obtained.

In accordance with the method described in Archives of Biochemistry and Biophysics 119, 41–49 (1967), it is possible to determine that the substituted antibody molecule carries 4 mercaptosuccinyl groups per molecule of antibody.

(c) Conjugate 12.4 ml of the solution of activated A chain of ricin (prepared in accordance with the technique of paragraph a), containing 1 mg/ml, that is to say 0.413 μmol, are mixed with 6.5 ml of a solution of anti-DNP antibodies carrying 4 mercaptosuccinyl groups (prepared in accordance with the method of paragraph b), containing 15 mg/ml, that is to say 0.658 μmol. The mixture is left to stand for 20 hours at ambient temperature and in the absence of light.

Spectrophotometric determination at 343 nm of the pyridine-2-thione liberated in the reaction medium indicates that 0.251 μmol of A chain has been coupled to 0.658 μmol of antibody. The preparation is dialysed against 3 times 5 liters of TPE for 75 hours at 5° C. and the resulting solution (17 ml) is filtered on a sterilising membrane (0.45 μm) and kept at −20° C. Purification is then carried out by filtration on Sephadex G 200 gel. For this purpose, 7 ml of the solution obtained above are centrifuged at 27,000×g for 10 mins and the supernatant liquid is treated with 0.6 ml of a solution of N-ethylmaleimide, containing 0.645 mg/ml in TPE, for 30 minutes, whilst standing at ambient temperature. The solution is filtered by the ascending technique on a column (diameter 26 mm) containing 473 ml of Sephadex G 200 gel. The product is eluted with TPE at a rate of 16 ml/hour and the effluent is collected in 2 ml fractions.

The concentration of the antibody in each fraction is measured by spectrophotometry at 280 nm and the concentration of the A chain is measured by means of its capacity for inhibiting acellular protein synthesis. The existence of 2 elution peaks, containing both the antibody and the A chain, is thus demonstrated and the fractions corresponding to each of these peaks are combined to give solutions a and b.

The conjugate, having a mean molecular weight which is greater than or equal to 800,000, corresponds to the first peak (solution a). This preparation corresponds to a conjugate originating from antibodies which have been polymerised by means of intermolecular disulphide bridges formed during the isolation of the antibody containing mercaptosuccinyl groups.

The second peak (solution b) consists of proteins, having a mean molecular weight of 190,000, corresponding to conjugates in which the antibody has not been polymerised.

The analytical determinations carried out make it possible to show that solution (a) contains 423 μg/ml of antibody and 20 μg/ml of A chain, that is to say an average of about 0.2 mol of A chain per mol of antibody. Likewise, solution (b) contains 171 μg/ml of antibody and 13 μg/ml of A chain, that is to say an average of about 0.4 mol of A chain per mol of antibody.

EXAMPLE 6

Preparation of the Conjugate Obtained From Anti-DNP Antibodies Substituted by Activated Sulphur Atoms and From the A Chain of Ricin (a) 3-(Pyrid-2-Yldisulphanyl)-Propionic Acid This product is obtained in two steps from 2,2′-dipyridyl disulphide without purification of the intermediate.

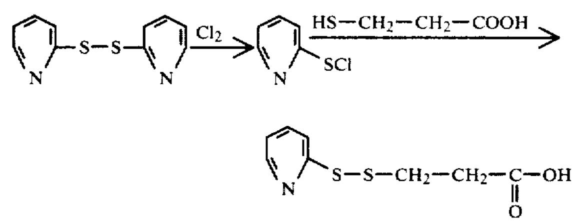

4 g of 2,2′-dipyridyl disulphide are dissolved in 25 ml of methylene chloride, and chlorine is bubbled into the solution for about 30 minutes. A precipitate forms during the reaction. The mixture is evaporated to dryness under high vacuum and the dry residue is used for the following operation.

2.4 g of 2-pyridine sulfenyl chloride are dissolved in 40 ml of methylene chloride, and a solution of 1.75 g of 3-mercaptopropionic acid in 10 ml of methylene chloride is added slowly, whilst stirring and cooling with an ice bath. When the addition is complete, the mixture is stirred at ambient temperature for 15 hours. 50 ml of water are added and the pH is brought to 4.5 by adding 1 N sodium hydroxide solution. The organic phase is separated off and dried over sodium sulphate and the solvent is evaporated off to dryness. An oily product remains and this crystallises (1.8 g). It is purified by dissolution in 16.8 ml of a 0.5 M aqueous solution of sodium bicarbonate. Activated charcoal is added, the solution is filtered and the expected product is then precipitated by adding concentrated acetic acid (0.5 ml) so as to bring the pH to between 3 and 3.5. The precipitate is filtered off and dried under high vacuum and a solid (1.3 g), melting point (capillary method): 62°–64° C., is obtained.

(b) Preparation of Activated Anti-DNP Antibodies

In order to alkylate any trace of a thiol group which could exist in the product used, 13 ml of a solution of anti-DNP antibodies, containing 23.6 mg/ml in a 0.1 M phosphate buffer, pH=7.0, are mixed with 1 ml of a solution of N-ethylmaleimide, containing 1.29 mg/ml in TPE. The mixture is stirred for 5 hours at ambient temperature and the solution is then dialysed continuously at 5° C. against TPE for 15 hours at a rate of 500 ml/hour.

The contents of the dialysis bag (12 ml containing 21.4 mg/ml) are mixed with 24 ml of water containing 19.9 mg of 1-ethyl-3-(3-dimethylaminopropyl)-carbodiimide, 55.7 mg of 3-(pyrid-2-yldisulphanyl)-propionic acid and 14 mg of 1-hydroxybenzotriazole. The mixture is stirred for 16 hours at ambient temperature and then centrifuged at 27,000×g for 10 minutes. The solution is dialysed continuously at 5° C. against TPE for 23 hours at a rate of 500 ml/hour. 34 ml of a solution containing 7.2 mg of protein per ml are thus obtained. By spectrophotometric determination at 343 nm of the pyridine-2-thione liberated by exchange with the reduced glutathione, it is found that an antibody carrying four activator groups per molecule of antibody has been obtained.

(c) Conjugate 16 ml of a solution of activated antibodies, containing 5.9 mg/ml and obtained as above, are mixed with 20 ml of a solution of A chain of ricin, containing 2.8 mg/ml in TPE. The mixture is left to stand for 24 hours at ambient temperature and in the absence of light. It is centrifuged at 27,000×g at 4° C. for 10 minutes.

Determination of the pyridine-2-thione liberated during the reaction indicates that 1.123 μmols of A chain have been coupled to 0.638 μmol of the antibody used, that is to say an average of 1.76 equivalents of A chain per mol of antibody.

The solution is dialysed continuously at 5° C. against TPE at a rate of 720 ml/hour for 21 hours. The contents of the dialysis bag (34 ml) are treated with 1 ml of a solution of N-ethylmaleimide, containing 12.5 mg/ml, for 5 hours at ambient temperature, and are then kept at −20° C.

This solution of conjugate is fractionated on a column of Sephadex G 200 gel under the conditions described in Example 5.

3 solutions are thus obtained:

solution (c) represents the conjugate of mean molecular weight 300,000, solution (d) represents the conjugate of molecular weight 190,000, and solution (e) represents the conjugate of molecular weight 160,000.

The composition of the conjugate in the various solutions obtained is described in the following table:

| | μg of A chain coupled to the antibody per ml of solution | Mols of A chain / Mols of antibody |
|---|---|---|
| solution c | 13 | 0.9 |
| solution d | 48 | 1.0 |
| solution e | 3 | 0.2 |

EXAMPLE 7

Preparation of the Conjugate Obtained from Anti-DNP Antibodies Substituted by an Activated Disulfide Group and from the A Chain of Ricin (a) 6-[3-(2-pyridyl disulphanyl)propionyl amino)]hexanoic acid This acid is obtained in two steps from 3-(2-pyridyl-disulphanyl) propionic acid without purification of the intermediate.

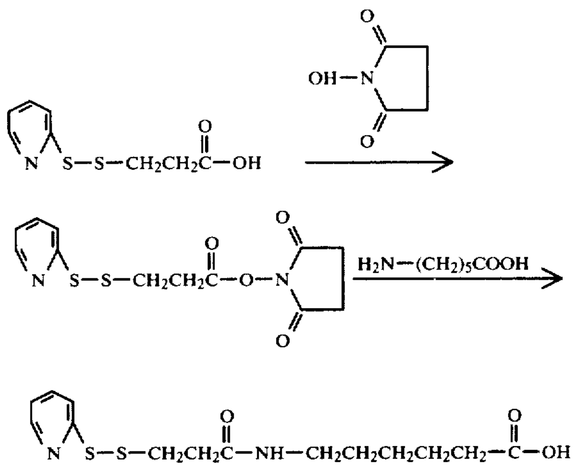

0.430 g of 3-(2-pyridyl disulphanyl) propionic acid obtained as described in example 6 a) is dissolved in 3 ml of pyridin. The solution is cooled in an ice bath. 0.230 g of N-hydroxysuccinimide in powder form and then 0.453 g of carbodiimid dicyclohexyl also in powder form are added to this solution. The mixture is stirred for 20 hours at 4° C. The reaction medium is filtered in order to remove the precipitate of dicyclohexylurea formed, and the precipitate is washed with pyridin. The washing solution is evaporated to dryness under high vacuum. The residue obtained is diluted in ethyl acetate. A new precipitate of dicyclohexylurea is formed; it is removed by filtering. The ethyl acetate is evaporated to dryness under high vacuum and subsequently, the washing operation with ethyl acetate is repeated twice. 0.610 g of the expected ester is thus obtained.

The product obtained is totally dissolved in 5 ml of tetrahydrofuran. Then 0.288 g of 6-amino caproic acid is added in solution with 2.5 ml of water. Triethylamine is added in stoichiometric quantity with respect to the 6-amino caproic acid (0.222 g) in order to maintain the pH at 7.0. The reaction is further carried out at 4° C. under stirring for 20 hours. The reaction medium is evaporated to dryness under high vacuum. The residue is diluted in 10 ml of water. The medium is acidified up to pH 4.5 by adding acetic acid. A precipitate is formed which is recovered by decantation and then solubilized in ethyl acetate. The solution is dried by magnesium sulphate, then filtered and evaporated to dryness under high vacuum.

0.600 g of the product to be purified is obtained. The purification is effected by division chromatography on a silica column, under the conditions defined by analysing the product in chromatography on thin layers in a ketone-chloroform-acetic acid mixture (15-80-5).

0.410 g of the product obtained is deposited on a column of internal diameter 2 cm containing 160 ml of silica gel (No. 60, 60-230 mesh MERCK) equilibrated with the chloroform. The elution is effected in discontinuous gradient of methanol in the chloroform. The pure product is eluted with the mixture containing 2% of methanol. The solvents are evaporated to dryness under high vacuum.

The product obtained, which is light yellow and of pasty consistence, is characterized by its spectrum of nuclear magnetic resonance.

(b) Preparation of Activated Anti-DNP Antibodies

To 9 ml of the solution of anti-DNP antibodies at a concentration of 11.4 mg/ml in the TPE buffer are added 9 ml of a water/t.butanol 2/1 (v/v) mixture containing 5.3 mg of 1-ethyl-3-(3-dimethylaminopropyl) carbodiimide, and 13.7 mg of 6-[3-(2-pyridyl disulphanyl]propiolamino) hexanoic acid. The operations are then effected as described in example 6.

The determination of the activated antibodies indicates an average substitution rate of 0.6 activator groups per mol of antibody.

The solution of antibodies thus obtained is concentrated by ultrafiltration up to 11.1 mg/ml.

(c) Conjugate 48.8 mg of modified antibodies are reacted with 35.6 mg of A chain of ricin at 7.9 mg/ml in TPE. The preparation is carried out under the conditions already described in example 6. The average coupling rate obtained is 0.5 A chain per mol of antibody. The purification of the conjugate by filtration is carried out as described in example 6.

EXAMPLE 8

Preparation of the Conjugate Obtained from the F(ab)'$_2$ Fragment of the Anti-DNP Antibody and from the A Chain of Ricin

(a) Preparation of Fragment F(ab)'$_2$ of the Anti-DNP Antibody

The solution of antibodies (example 4) is dyalised against the 120 mM acetate buffer, pH=4.7. To 45 ml of this solution containing 500 mg of antibodies are added 3 ml of a solution of pepsine at a concentration of 10 mg/ml in the same buffer (E.C. 3.4.4.1. pork pepsin, twice crystallised, at 3200 $\mu$/mg-SIGMA). Incubation is maintained for 20 hours at 37° C. The progress of the hydrolysis is checked by electrophoresis in the presence of sodium dodecyl sulphate [(J. Biol. Chem. 244, 4406–4412, (1969)] by the disappearance of the strip containing 150,000 dalton and corresponding to the non-hydrolysed antibody.

The hydrolysis is stopped by adjusting the pH of the reaction medium to 7.0 with the aid of a solution of 1 N sodium, then the solution is centrifuged and the insoluble removed. The centrifugation supernatant is deposited on a column of internal diameter 50 mm containing 1800 ml of Sephadex G 150 ® equilibrated with the 100 mM phosphate buffer, pH=7.0.

The elution is effected with the same buffer: the first peak obtained is collected in two fractions: the first one (200 ml) contains 70 mg of F(ab)'$_2$ fragment of the antibody, and the second (100 ml) contains 70 mg of a mixture of an F(ab)'$_2$ fragment with a contaminating fragment of 50,000 dalton molecular weight. The second peak contains protein fragments which an average molecular weight of 10,000 dalton. It is removed.

The fragment F(ab)'$_2$ obtained pure in the first fraction of the first peak is concentrated by ultrafiltration (procedure described in example 1) up to a concentration of 16 mg/ml and stored at −20° C.

The fragment F(ab)'$_2$ thus obtained shows the following characteristics:

Molecular weight: 95,000 dalton (determined after calibration of the Sephadex G 150 ® gel)

Isoelectric point: between pH 7.7 and 8.8 (obtained by isoelectrofocalisation on LKB plate).

(b) Preparation of the Activated Fragment F(ab)'$_2$

To 15 ml of the F(ab)'$_2$ solution at a concentration of 15.6 mg/ml are added 15.3 ml of a mixture of water/t.butanol 2.1 (v/v) containing 17.3 mg of 1-ethyl 3-(3-dimethylaminopropyl) carbodiimide and 50.4 mg of 3-(2-pyridyl disulphanyl)propionic acid. The mixture is incubated at 30° C. for 20 hours. The solution is then dialysed continuously against the TPE buffer at 4° C. for 23 hours at a rate of 500 ml/hour. Spectrophotometric determination at 343 nm of the pyridine 2-thione liberated by exchange with the reduced glutathione indicates that the activation of fragment F(ab)'$_2$ has lead to an average substitution rate of 1.5 activator groups per mol of F(ab)'$_2$.

The solution of activated F(ab)'$_2$ thus obtained is concentrated by ultrafiltration up to 10 mg/ml.

(c) Conjugate

To 13.8 ml of the solution containing 10 mg/ml of activated F(ab)'$_2$ obtained as described above are added 13.8 ml of solution of A chain of ricin at 8 mg/ml in the TPE buffer.

The mixture is incubated at ambient temperature for 24 hours in a nitrogen atmosphere and in the absence of light. The solution is then centrifugated at 27000×g, at 4° C. for 10 minutes and the supernatant is recovered. Determination of the pyridine 2-thione liberated during the reaction indicates that the average coupling rate is 1.2 equivalents of A chain per mol of F(ab)'$_2$.

The solution is deposited on a column with internal diameter 50 mm containing 1730 ml of Sephadex G 200 ®. Elution is carried out with the TPE buffer. The fractions are collected under a volume of 8.4 ml and the analysis of the fractions is carried out as described in examples 5 and 6. The conjugation product comes out into a peak.

The fractions constituting the peak of the conjugate are grouped into three solutions, respectively as follows:

solution f: front part of the peak
solution g: central part of the peak
solution h: tail of the peak The analysis of solution g by determination of its inhibitory activity of the protein synthesis (test 1) and the determination of the proteins give the following results:

|  | $\mu$g of A chain coupled to F(ab)'$_2$ per ml of solution | Equivalents of A chain per mol of F(ab)'$_2$ |
| --- | --- | --- |
| Solution g | 148 | 1.4 |

(d) Concentration of the Conjugate

In a first step, the concentration is carried out by ultrafiltration: 255 ml of solution g of the conjugate (at 148 $\mu$g/ml of A chain) are thus concentrated to 381 $\mu$g/ml. The solution is then diluted 10 times in distilled water so as to lower the ionic strength of the medium.

The solution obtained (400 ml at 38 $\mu$g/ml of A chain) is deposited on a column of internal diameter 9 mm containing 5.7 ml of C.M. Sepharose ® equilibrated with the 10 mM phosphate buffer, pH=6.5 mixed with disodium salt of 1 mM ethylene diaminotetracic acid.

The depositing is carried out at a rate of 80 ml/hour. Under these conditions, the total conjugate becomes fixed on the column. When depositing is completed, 4.5 ml of the same buffer are left free, and elution of the conjugate is effected with the TPE buffer at the same rate.

The conjugate comes out into a single peak. The tail of the peak containing little proteins is removed. The remaining fractions are grouped and the concentration in A chain is determined.

Determination indicates that the concentration operation on C.M. Sepharose ® has allowed the concentration of A chain of the conjugate to be brought to 3.6 mg/ml. The operation is quantitative and the fractions constituting the solution at 3.6 mg/ml is overall 76% of the quantity of the conjugate deposited on the column.

EXAMPLE 9

Preparation of the Conjugate Obtained from Anti-Thy 1.2 IgM Antibody and from the A Chain of Ricin (a) Preparation of the Anti-Thy 1.2 IgM Antibody The pure IgM is prepared from the ascites liquid obtained from OLAC LTD (Thy 1.2 F7 D5 monoclonal IgM cytoxic antibody).

To 50 ml of ascites liquid containing the antibody are added 15 g of powdered ammonium sulphate. After dissolution, the mixture is incubated for one hour at 4° C. and the whole is then centrifugated for 20 minutes at $17000 \times g$.

The supernatant after centrifugation is removed.

The deposit is dissolved in 20 ml of 100 mM phosphate buffer, pH=7.0, then the solution is dialysed continuously against 10 liters of the same buffer. The solution obtained is deposited on a column of internal diameter 50 mm containing 1800 ml of Sepharose 6B ® equilibrated with the 100 mM phosphate buffer, pH=7.0. Elution is carried out with the same buffer: the first peak obtained corresponds to IgM aggregates. The second peak obtained is collected in two fractions: the first fraction (from the front part to the top of the peak) is constituted by pure IgM; the second fraction contains a mixture of IgM with a contaminating protein of molecular weight estimated at about 660,000 dalton. This second fraction is again treated with ammonium sulphate and the precipitate obtained is centrifugated and re-dissolved in the 100 mM phosphate buffer, pH=7.0. The solution obtained is deposited on the Sepharose 6B ® column suitably washed after the first operation. Elution by the 100 mM phosphate buffer, pH=7.0 gives rise, as in the first operation, to the production of two peaks. The second peak obtained contains pure IgM. Each of both filtration operations on Sepharose 6B ® has thus permitted a fraction containing pure IgM to be obtained. These two fractions are brought together and the whole is treated with ammonium sulphate at a final concentration of 300 mg/ml, at 4° C. The preparation is centrifugated for 20 minutes at $17000 \times g$, then the deposit is diluted in the 100 mM phosphate buffer, pH=7.4 and mixed with 400 mM sodium chloride.

All these operations make it possible to prepare 8 ml of a solution containing 6.4 mg/ml of pure IgM. Analysis by electrophoresis in the presence of sodium dodecyl sulphate has been used for characterizing the fraction: the pure IgM thus obtained shows after analysis two very similar bands of equal intensity corresponding to molecular weights approximating 900,000 dalton.

(b) Preparation of the Activated Anti-Thy 1.2 Antibody

To 7.6 ml of the solution of IgM at a concentration of 7.0 mg/ml are added 0.46 ml of a mixture of water/t-.butanol 1/5 (v/v) containing 2.9 mg of 1-3(3-dimethylamino propyl) carbodiimide ethyl and 7.7 mg of 3-(2-pyridyl disulphanyl)propionic acid. The mixture is incubated for 20 hours at 30° C. The solution is then dialysed continuously against the 100 mM phosphate buffer, pH=7.4, mixed with 400 mM sodium chloride and disodic salt of 1 mM ethylendiaminotetracetic acid. The dialyis is continued for 23 hours at 4° C. at the rate of 500 ml/hour. The solution is subsequently centrifugated at $27000 \times g$ at 4° C. for 10 minutes and the supernatant is recovered. Spectrophotometric determination at 343 nm of the pyridine 2-thione liberated by exchange with the reduced glutathione shows that the activation of the antibody has resulted in the average substitution rate of 13 activator groups per mol of IgM.

(c) Conjugate

The solution of A chain obtained as described in Example 2 is dialysed continuously against the 100 mM phosphate buffer, pH=7.4, mixed with 400 mM sodium chloride and disodic salt of 1 mM ethylenediaminotetracetic acid. The dialysis is conducted at a rate of 500 ml/hour for 20 hours at 4° C.

To 6.8 ml of the solution of activated IgM obtained as described above are added 3.9 ml of dialysed A chain, at a concentration of 7.4 mg/ml. The mixture is incubated for 24 hours at ambient temperature in an nitrogen atmosphere and in the absence of light. The determination of the pyridine 2-thione liberated during the reaction indicates indicates that the average coupling rate is 9.7 equivalents of A chain per mole of IgM.

The solution is deposited on a column of internal diameter 50 mm containing 1727 ml of Sepharose 6B ® equilibrated with the conjugation buffer. Elution is conducted with the same buffer. The fractions are collected under a volume of 3.7 ml and the analysis of the fractions is carried out as described in examples 5 and 6. The conjugation product comes out into two peaks: The first corresponds to the conjugate with an average molecular weight higher than that of the IgM. The second peak corresponds to the conjugate with an average molecular weight approximately equivalent to that of the IgM. The central part of this peak (solution i) is retained. The composition of the conjugate of solution i corresponds to the following characteristics:

|  | μg of A chain coupled to IgM per mol of solution | Equivalents of A chain per mol of IgM |
|---|---|---|
| Solution i | 23.7 | 3.2 |

The conjugates according to the invention and also the compounds used in the preparation of the said conjugates, were studied with respect to their biological properties, and very particularly, their carcinostatic action. An account of the principle of the various tests used is given below.

IN VITRO TESTS

(1) Inhibition of Protein Synthesis

The fundamental biological property of the A chain of ricin is to inhibit microsomal protein synthesis by damaging the ribosomal 60S sub-unit.

(a) Acellular Model (Test 1)

The in vitro procedure corresponding to a noncellular protein synthesis model uses subcellular fractions of rat liver, which are suitably complemented and capable of incorporating $^{14}C$-phenylalanine in the presence of an artificial messenger RNA, namely polyuridylic acid.

The method of operation employed for preparing the subcellular fractions and for measuring the incorporation of $^{14}C$-phenylalanine is an adaptation of the method described in Biochemica Biophysica Acta 312, 608–615 (1973), employing both a microsomal fraction and a cytosol fraction of rat hepatocytes. The sample containing the A chain is introduced in the form of a suitably diluted solution in a 50 mM TRIS-HCl buffer, pH=7.6, containing 0.2% of 2-mercaptoethanol and 15 μg/ml of bovine serum albumin.

From the counting data, the percentage inhibition of the incorporation of $^{14}C$-phenylalanine in the proteins, for each reaction medium containing the A chain of ricin, is calculated relative to a control medium without inhibitor.

From these results, it is possible to calculate that concentration of the A chain in the reaction medium which inhibits the incorporation of radioactivity into the proteins by 50%. This 50% inhibitory concentration (IC 50) makes it possible to characterise any preparation containing the A chain.

The same procedure also makes it possible to determine the A chain present in a sample by comparing the percentage inhibition, shown by this sample, with a standard curve obtained under the same conditions using solutions having a known concentration of pure A chain.

(b) Cellular Model (Test 2)

This test measures the effect of the substances studied on the incorporation of $^{14}C$-leucine into cancerous cells in a culture.

The cells used are HeLa cells which originate from a biopsy of human cervical adenocarcinoma and are kept in a continuous line by means of monolayer culture.

These cells are incubated in the presence of preparations of the substances to be studied and are then subjected, after incubation, to a measurement of their degree of incorporation of $^{14}C$-leucine. This measurement is carried out in accordance with a technique adapted from the technique described in Journal of Biological Chemistry 249 (11), 3,557–3,562 (1974), using the tracer $^{14}C$-leucine for determining the degree of protein synthesis. Determination of the incorporated radioactivity is effected in this case on the whole cells isolated by filtration.

From these determinations, it is possible to plot the dose/effect curves showing, on the abscissa, the concentration of the substances studied, and, on the ordinate, the incorporation of $^{14}C$-leucine, expressed as a percentage of the incorporation by the control cells in the absence of the substance to be studied.

The concentration which inhibits the incorporation of $^{14}C$-leucine by 50%, or the "50% inhibitory concentration" (IC 50), can thus be determined for each substance studied. It was shown that the measurement of incorporation of $^{14}C$-leucine in the whole cells resulted in the determination of IC 50 values which are identical to those obtained by the conventional method of protein synthesis measurement.

If it is desired to study conjugates prepared with the anti-DNP antibodies, the HeLa cells must be able to be recognised by these antibodies and must therefore carry hapten units on their surface. The HeLa cells are hence converted into target cells by labelling with a suitable hapten. In practice, it was decided to use the 2,4,6-trinitrophenyl group, or TNP, as the hapten. The fixation of the TNP groups to the HeLa cells is effected by the action of 2,4,6-trinitrobenzenesulphonate (TNBS) in accordance with an adaptation of the techniques described in Biochimica Biophysica Acta 255, 79–90 (1972) and Journal of Immunology 111, 930–937 (1973).

The modification of the method essentially consists in choosing the reaction parameters, namely a temperature of 4° C. and stopping the reaction with an excess of lysine after a reaction time of 15 seconds.

This labelling was retained for various reasons namely:

the low toxicity of TNBS to the HeLa cells, the high level of cross-reaction between DNP and TNP, and comparable levels of incorporation of $^{14}C$-leucine between labelled cells and unlabelled cells.

The concentration of TNBS in the reaction medium (10 mg/ml) causes the fixation, to each cell, of $7.10^7$ hapten units accessible to the antibodies. The association constant between anti-DNP antibodies and hapten units is $1.2 \cdot 10^7$.

For the conjugate with anti-Thy 1.2 specificity, the cells used belong to the WEHI-7 line (lymphoma of Balb/C mice) obtained from SALK INSTITUTE—SAN DIEGO (California). These cells are not subjected to any labelling step because they naturally carry the Thy 1.2 antigen on their surface. Incubation with the conjugate and then measurement of the degree of protein synthesis are effected as described above.

(2) Hemagglutination

The hemagglutination test (Journal Of Biologival Chemistry 249, 803 (1974) is intended for comparing the capacity of the various preparations studied to become fixed to the membrane of human blood cells of group O, Rhesus negative.

The test can be:

either direct (test 3), by bringing the substance to be studied into contact with red blood cells, which leads, depending on the dose of substance, to a negative or positive response, or indirect (test 4). In this case, after the direct test, the detection of the substance which may be fixed to the red blood cells is sensitised by adding, to the red blood cells separated from the reaction medium by decantation, an immune serum containing antibodies which are capable of recognising the substance studied, and the inherent hemagglutinant activity of which has been removed by adsorption onto red blood cells of the same group.

IN VIVO TESTS

(1) Acute Toxicity (Test 5)

The study of the acute toxicity is carried out by the intraperitoneal or intravenous injection of the substance to be studied, brought into isotonic solution, to batches of animals. The animals are observed for 7 days and the mortality is noted for each dose studied. The 50% lethal dose (LD 50) is then determined.

(2) Effect of the Conjugates on the Development of Cancerous Cells

The model chosen consists in studying the effect of the substances to be tested on the development, in the form of solid tumours, of cancerous cells injected into the animal.

The experimental method consists in injecting HeLa cells, carrying the hapten TNP, into "nude" mice (Bomlholtgaard congeneric nude/nude mice), known for not rejecting allogenic or xenogenic grafts, and in treating these mice by simultaneous or subsequent injection with the compound to be studied.

Various tests were carried out:

(a) Test 6: Pre-incubation of the HeLa-TNP cells with the conjugate, followed by subcutaneous injection into the animal.

The size of the tumours which may have developed is then determined by measuring 2 orthogonal diameters of the tumour in accordance with the technique described in Annales d'Immunologie (Institut Pasteur) 124 C, 567–572 (1973).

(b) Test 7: Intraperitoneal injection of the HeLa-TNP cells, followed by the injection, also into the intraperitoneal cavity, of the compound to be studied.

At the end of the experiment, the size of the tumours is determined, after sacrificing the animals, by measuring the weight of the tumours which have been collected.

The various in vitro and in vivo tests thus described were used for studying the properties of the conjugates and also of the substances used for the preparation of the conjugates.

RICIN AND A CHAIN

The ricin and the A chain were subjected to the various in vitro tests and also to the in vivo toxicity test. Furthermore, the A chain purified by concentration step on C. M. Sepharose (indicated by $(A)_p$ chain in the table) has been subjected to the same tests.

The results obtained are given in Table I.

These results indicate that ricin possesses a strong capacity for inhibiting protein synthesis, both in an acellular system and in a cellular system. In an acellular medium, the A chain also strongly inhibits protein synthesis but, on the other hand, it cannot exert its effect in a cellular medium when it is separated from the B chain.

The same phenomenon is observed in the hemagglutination tests and the acute toxicity test, in which tests ricin proves to be much more active than the A chain.

These results furthermore indicate that the concentration step on C. M. Sepharose makes it possible to again reduce the non-specific toxicity of the A chain by substantially increasing the pureness of the preparation. The extra pure A chain thus produced is free of non-specific toxicity with respect to a cellular system. This is clearly shown by the activity ratio between ricin and the $(A)_p$ chain in this test, which is higher than 10000.

Exhaustive absorption tests of the A chain were conducted using successively excesses of HeLa cells and red blood cells which have been brought into contact with the A chain, and by measuring the cellular toxicity of the A chain in the absorption supernatant (test 2):

The cellular toxicity of the solution of A chain not concentrated on C. M. Sepharose is lowered by absorption and thus brought to the toxicity level of the solution of A chain which is concentrated on C. M. Sepharose and not absorbed.

On the contrary, the toxicity of the preparation concentration on C. M. Sepharose is no longer lowered by the absorption tests, which confirms the total lack of affinity of the $(A)_p$ chain thus prepared towards the plasma membranes of the cells, and consequently the extreme degree of pureness obtained.

ANTI-DNP ANTIBODIES

In the test for the inhibition of protein synthesis in a cellular system, the anti-DNP antibodies do not produce any effect up to the highest concentration tested, namely $10^{-6}$ M.

Furthermore, in the acute toxicity test, no indication of toxicity was recorded up to the highest dose tested, namely 1.6 mg of antibody per animal.

CONJUGATES

The purpose of a first series of experiments is to show the integrity of the properties of the A chain, on the one hand, and of the antibody, on the other hand, in the conjugates prepared.

First of all, by means of radioimmunological test (Handbook of Experimental Immunology, Volume 1, chapter 15, pages 1 to 18, Publisher D. M. WEIR, 2nd edition, 1973), it was possible to establish that the anti-DNP antibody activity of the conjugate was equivalent to the activity of the antibody by itself.

Furthermore, as regards the A chain of the conjugate, the inhibitory activity with respect to a-cellular protein synthesis was determined, on the one hand, on a sample of conjugate (Example 4, solution a), and, on the other hand, on another identical sample, incubated for 30 minutes with a 0.2% strength solution of 2-mercaptoethanol in order to split the disulphide bridge.

An IC 50 of 59.4 ng/ml of A chain was obtained in the 1st case and an IC 50 of 9.2 ng/ml of A chain was obtained in the second case, this being an activity ratio of 1 to 6.6.

This shows that the main part of the inhibitory activity with respect to protein synthesis only appears after the conjugate has been treated with 2-mercaptoethanol in order to break the disulphide bond created.

The fact that an inhibitory activity is detectable without treatment with 2-mercaptoethanol does not contradict this conclusion insofar as the medium used for determination contains thiols which are partly involved in the liberation of the A chain coupled to the antibody.

In conclusion, the conjugates obtained according to the invention retain the properties of each of their constituents.

The purpose of another series of tests is to determine the therapeutic effectiveness of the conjugates.

(a) Effect On The Cellular Model (Test 2)

Figure 2:
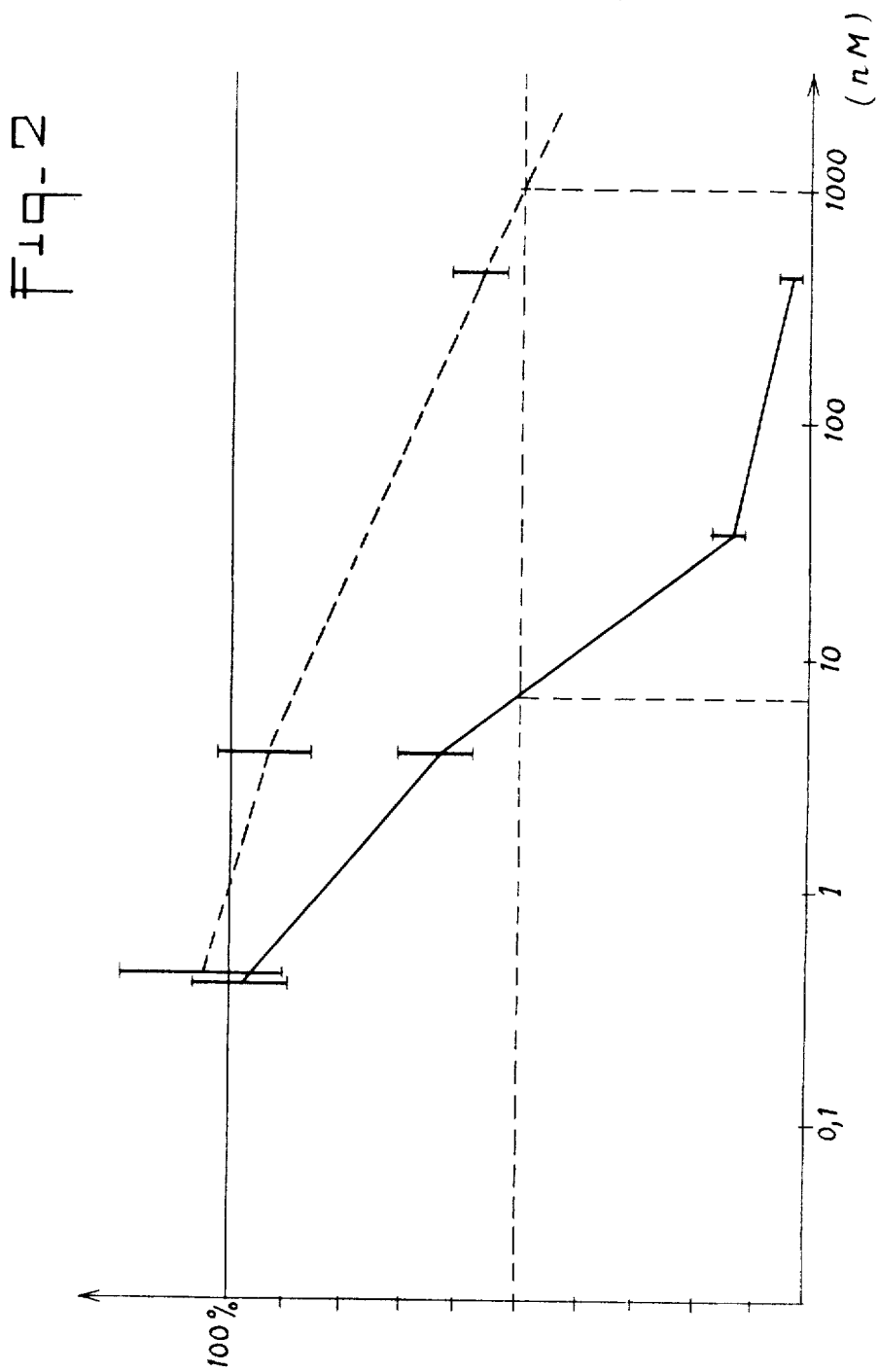

FIGS. 1 and 2 give the curves showing the percentage inhibition of incorporation of $^{14}C$-leucine by the TNP-labelled HeLa cells, as a function of the dose of conjugate used, expressed in concentrations (nM) of A chain. The conjugate used in these figures is the conjugate of anti-DNP antibodies and of the A chain such as described in Examples 5 and 6. By way of comparison, the action of the conjugate on unlabelled HeLa cells is also shown (broken lines).

These curves were obtained, for FIGS. 1 and 2 respectively, with the conjugate of Example 5 (solution (b) and with the conjugate of Example 6 (solution (e). These curves show that the 50% inhibitory effect with respect to cellular protein synthesis of the HeLa-TNP cells is obtained for concentrations (IC $50 = 11 \times 10^{-9}$ M. in the case of solution b and $7.5 \times 10^{-9}$ M in the case of solution (e) which are very much lower than those required to obtain the same effect with unlabelled HeLa cells (IC $50 = 130 \times 10^{-9}$ M in the case of solution b and $1000 \times 10^{-9}$ M in the case of solution (e).

Furthermore, if bovine serum albumin—DNP (1 mg/ml) is added to the incubation medium, the inhibitory effect of the conjugate is entirely cancelled.

Figure 3:
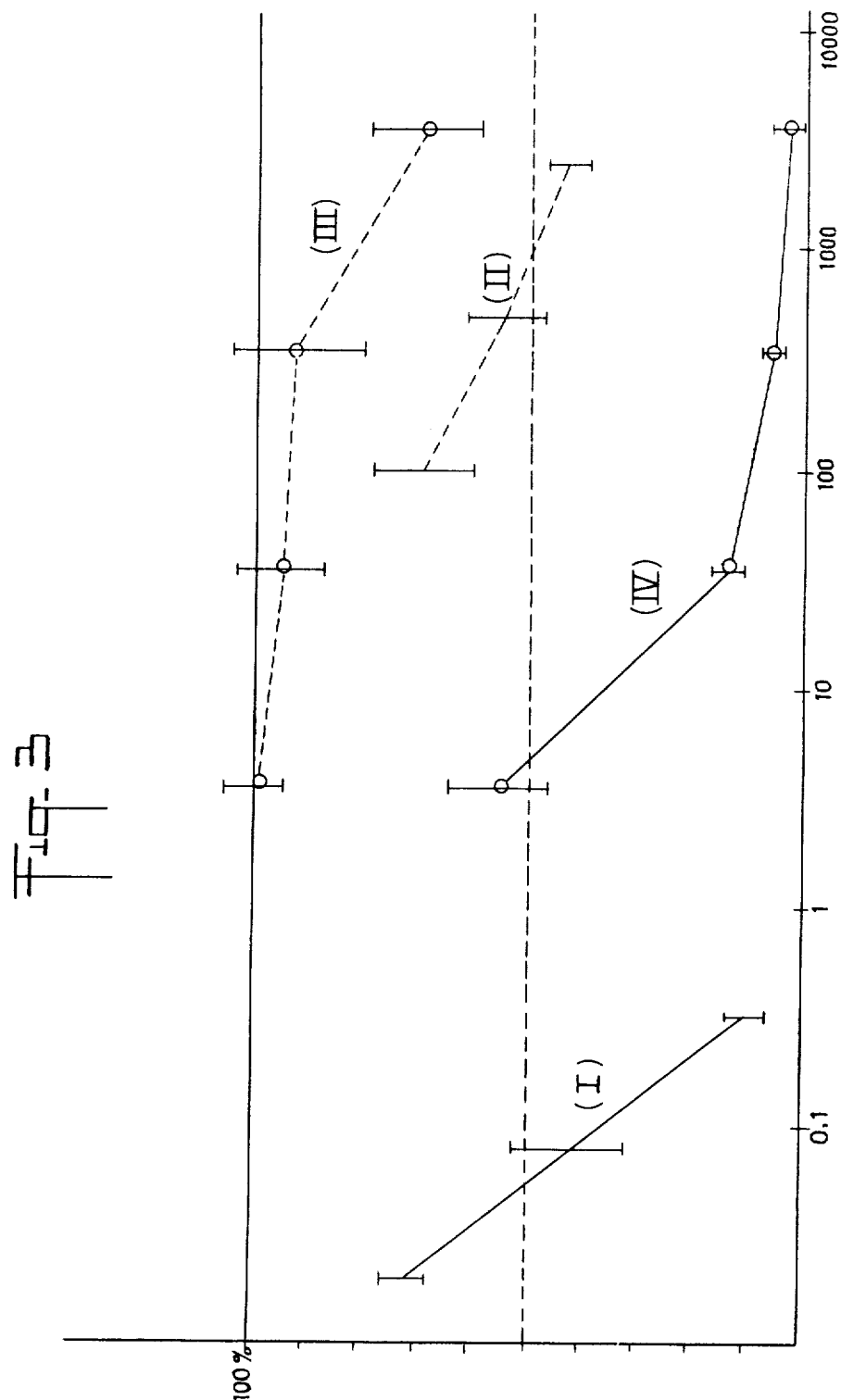

FIG. 3 shows the results obtained with the conjugate formed from the A chain of ricin and the F(ab)'$_2$ fragment of anti-DNP IgG. The data are the same as those of FIGS. 1 and 2. The results are given for:

(I) ricin Ic 50 (in A chain) 5.5. $10^{-11}$ M.

(II) the A chain IC 50 9. $10^{-7}$ M.

(III) the conjugate on HeLa IC 50 cannot be determined $> 10^{-5}$ M.

Figure 4:
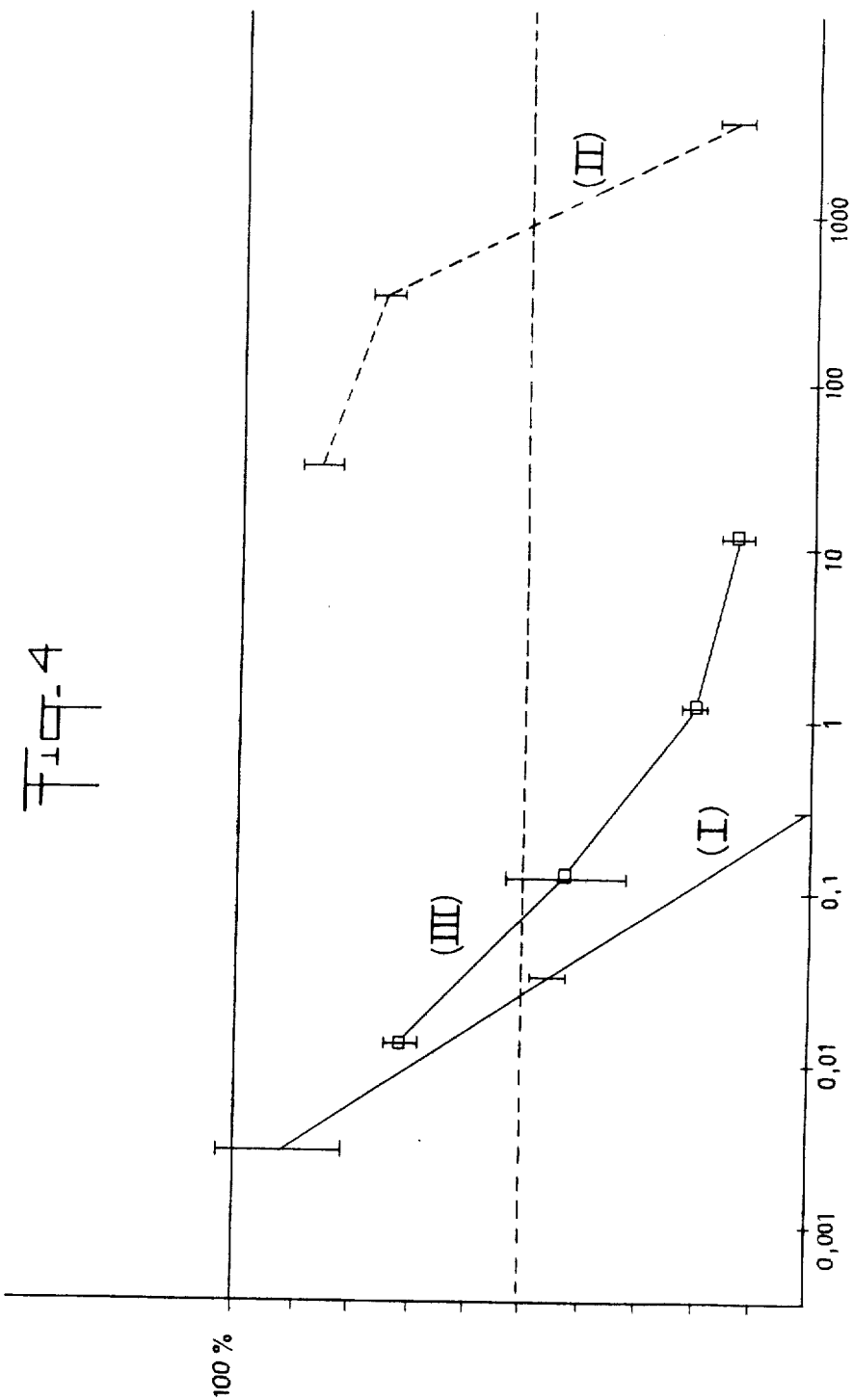

FIG. 4 shows the inhibition of the incorporation of $^{14}$C into WEHI-7 cells by using the conjugate formed from the A chain and the anti-Thy 1.2 IgM. The data are the same as those of FIGS. 1 and 2. The results are given for:

(I) the ricin IC 50 (in A chain) 2.4. $10^{-11}$ M (II) the A chain IC 50 8.1 $10^{-7}$ M (III) the conjugate IIC 50 (in A chain) 5.2. $10^{-11}$ M Finally, it should be noted that the conjugate formed from the A chain of ricin and the anti-DNP IgG by using 6-[3-(2-pyridyl disulphanyl)propionylamino]hexanoic acid as the activator of IgG, has a toxicity and a specificity identical to those of the conjugate prepared in Example 6.

It can be concluded that the conjugates prepared according to the invention have a specific action. By administering a suitably chosen dose of the conjugate, it is possible to act only on the cells which carry the antigen corresponding to the antibody used.

The formation of a disulphide bridge between the A chain and an antibody specific of an antigen, which is naturally carried by cancerous cells, makes it possible to destroy the cancerous cells with a very high efficiency and an important specificity of action.

(b) In vivo tests

A. Tests conducted on the conjugate of A chain and of anti-DNP antibody (solutions c and d, Example 6)

(1) Test 6 described above was used with HeLa-TNP cells, at a concentration of $10^5$ cells per ml, incubated for 90 minutes at 37° C. with the conjugate (solution c), at a concentration of $10^{-8}$ M expressed in terms of A chain.

After centrifugation (700 × g, 10 minutes), the deposit is re-suspended in PBS (a buffered isotonic solution without calcium or magnesium, J. Exp. Med. 99 167 (1954)) at a concentration of $10^7$ cells per ml. The animals (14 weeks old) receive 0.1 ml of this suspension, that is to say $10^6$ cells, by subcutaneous administration.

A control batch receives cells not incubated with the conjugate.

The animals are observed daily and this is accompanied by measurement of the surface area of the tumours. Any tumour of which the surface area is greater than or equal to 10 mm$^2$ (sensitivity limit of the test) is considered to have taken.

Figure 5:
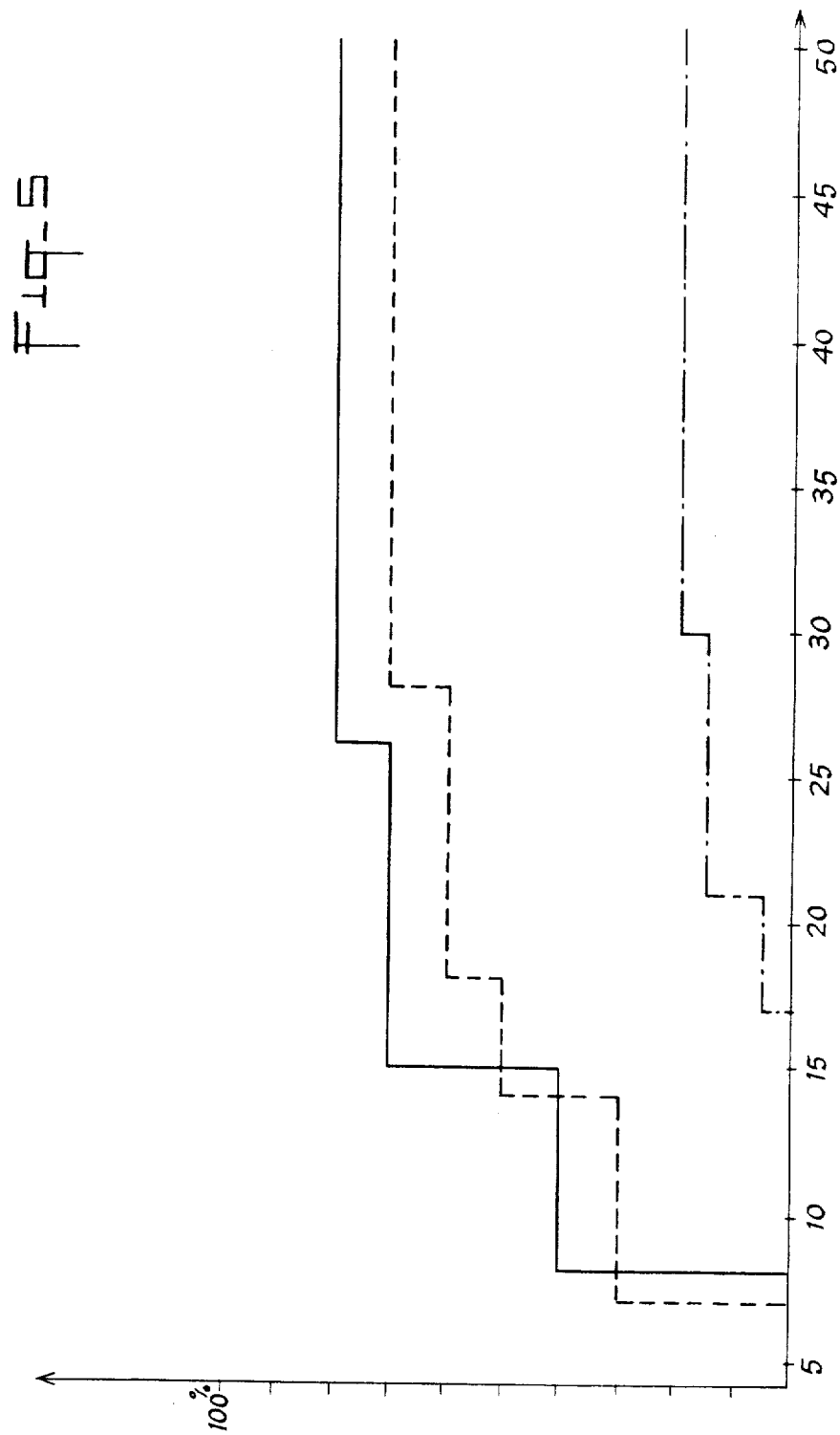

FIG. 5 represents the cumulative percentage of developed tumours having a surface area $\geq 10$ mm$^2$, as a function of time, after having injected, into the mice, either HeLa cells (curve in solid line) or TNP-labelled HeLa cells (curve in broken lines) or HeLa cells labelled with TNB and pre-incubated with the conjugate (curve in broken lines and dotted lines). The effectiveness of the conjugate, which strongly reduces the development of tumours, can be established from the figure.

Observation up to the 50th day shows the development of tumours in 80% of the cases for HeLa cells which have not been treated with the conjugate, and in 70% of the cases for the HeLa-TNP cells which have not been treated with the conjugate.

This percentage is only 20% in the case of HeLA-TNP cells which have been pre-incubated with the conjugate.

The difference is statiscally significant at the 5% level.

(2) Test 7 is used by the intraperitoneal injection, into the animals (10 weeks old), of 2.10$^6$ HeLa-TNP cells suspended in 0.1 ml of a culture medium.

0.1 ml of conjugate, containing 36 μg of A chain (solution d concentrated 7.5 times by ultrafiltration) is then injected.

A control batch receives the same injection of HeLa cells but does not receive any treatment with the conjugate.

On the 25th day after the start of the experiment, the animals are sacrificed and the tumours are weighed.

Figure 6:
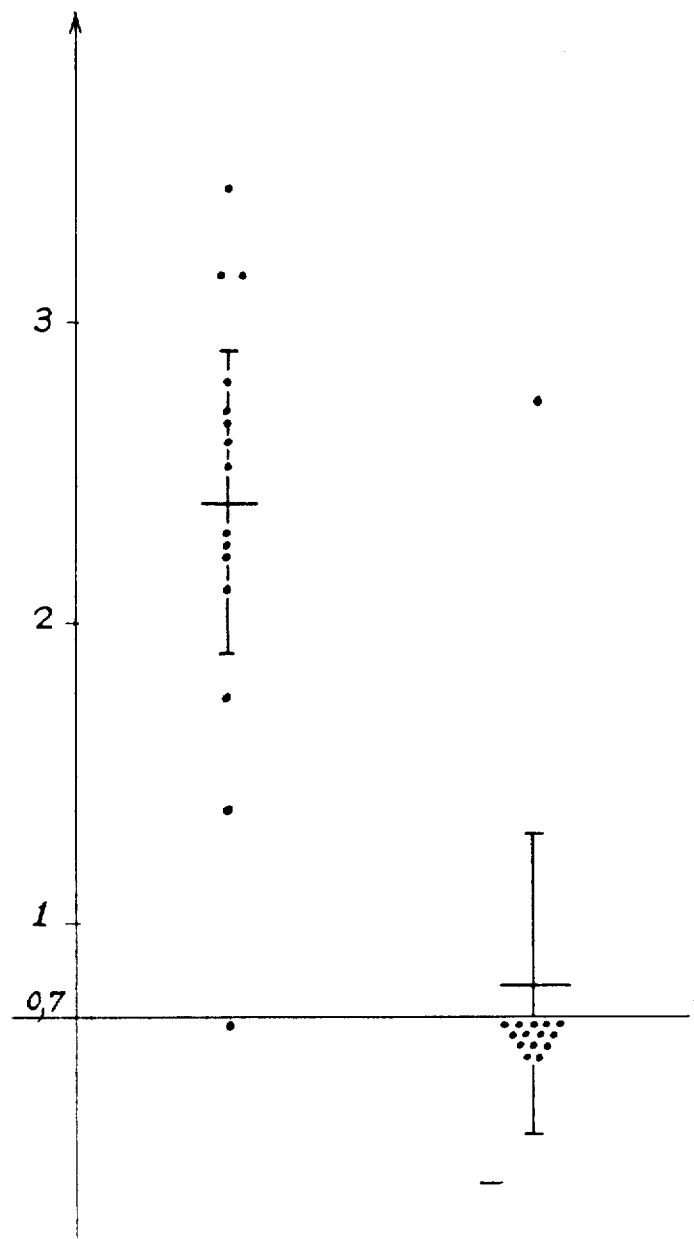

FIG. 6 shows the decimal logarithm of the weight of the tumours in mg for each of the animals of the two batches, the control animals being on the left and the treated animals being on the right. The threshold of detection is 5 mg, this corresponding to a decimal logarithm of 0.7.

From this figure, it can be established that, in the case of the control batch, tumour development occured in 14 cases out of 15 (14 points above the threshold of detection and only 1 point below). Conversely, in the case of the treated animals, tumour development only occured in 1 case out of 15 (only 1 point above the threshold of detection).

B. Tests conducted on the conjugate of the A chain and of the anti-Thy 1.2 antibody (solution i, Example 9).

The cancerous cells used are of the WEHI 22. 1 line (obtained from SALK INSTITUTE, SAN DIEGO, Calif.) and originate from a lymphoma of Balb/C mice. They are injected into Balb/C mice obtained from BOMHOLTGAARD (Denmark) and are kept from their birth and for the duration of the test in a zone free of specific pathogenic organisms (SPF).

In the test, the WEHI 22.1 cells kept in continuous culture are collected on the third day after transplant of the culture, washed by centrifugation and resuspended in an isotonic phosphate buffer (PBS) at a concentration of 12.10$^6$ cells/ml.

0.2 ml of the suspension is injected by intraperitoneal administration into mices previously placed at random in their cages and carrying an individual marking on their feet.

In mice not treated with the conjugate, the intraperitoneal injection of WEHI 22.1 cells is followed by the evolution of these cells into tumours dispersed in the peritoneum with formation of an ascites. This evolution of the cells is accompanied with an increase in the body weight. The ascites is detected by observing an increase in the abdominal volume.

One hour after injection of the cells, the animals treated with the conjugate receive 1 ml of solution of the conjugate (solution i, 23.7 mg/ml of A chain) by intraperitoneal administration, previously dialysed extensively against the PBS buffer, and then sterilized by filtration. The batches of control animals receive 1 ml of PBS buffer containing no conjugate.

On the 7th day after inoculation of the cells, the treated animals receive a second injection of the conjugate in the same conditions, and the control animals a second injection of PBS buffer.

Figure 7:
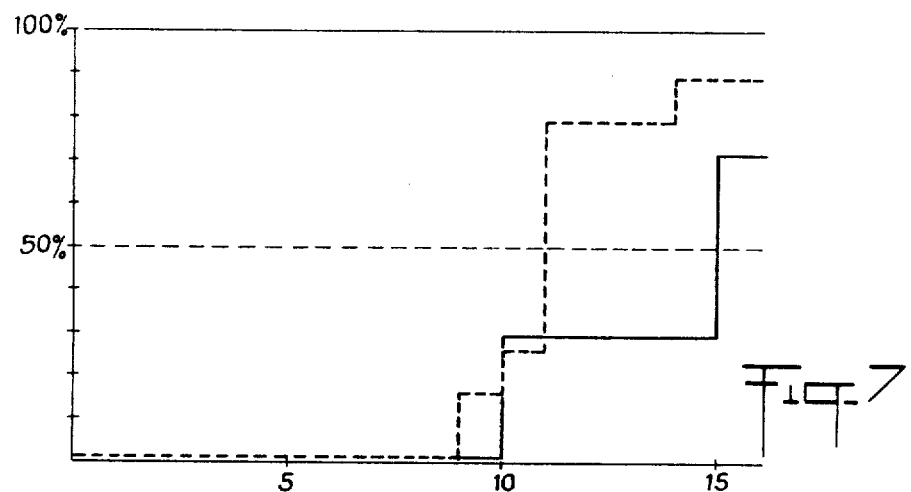
Figure 8:
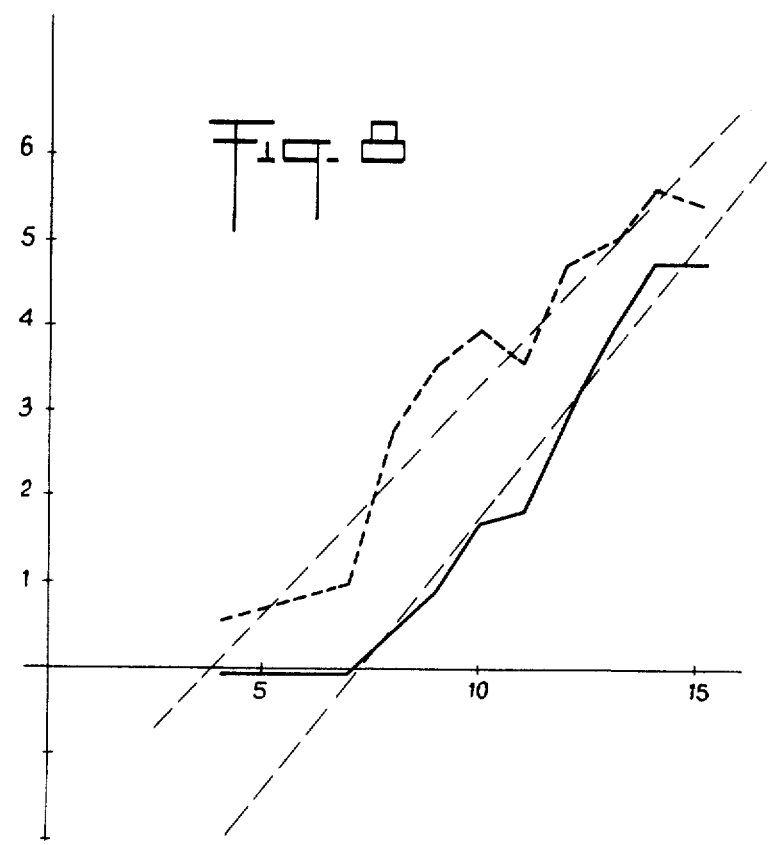

The results of the test are seen in FIGS. 7 and 8. FIG. 7 describes the chronology of the formation of ascites in the treated and in the non-treated animals. FIG. 8 describes the evolution of the body weight in treated and in non-treated animals. The evolution of the weight is expressed in terms of weight increase (grams) with respect to the weight of the same animals 3 days before inoculation of the cells.

FIG. 7 (abcissa representing the number of days after inoculation of the WEHI 22.1 cells, and the ordinate representing the percentage of animals showing an ascites) shows the existence of an inhibition of the formation of ascites in animals treated with the conjugate. This inhibition is proved by the ascites forming at different times (curve in continuous line representing the treated animals, and that in dotted line representing the non-treated animals).

FIG. 8 (abcissa representing the number of days after inoculation of the WEHI 22.1 cells and the ordinate the average increase (grams) in the body weight), also shows an inhibition of the increase in the body weight in animals treated with the conjugate (continuous line) compared with the control animals (dotted line).

These observations are confirmed by the statistical analysis of the results:

The inhibition by the conjugate of the formation of ascites is significant at the 1% threshold of reliance (test X2).

The inhibition by the conjugate of the weight increase is significant at the 5% threshold of reliance (test of comparison of the gradients of linear adjustments).

The in vivo test makes it possible to demonstrate the anti-cancerous activity of the conjugate formed from the A chain of ricin and the anti-Thy 1.2 IgM. Such activity is shown by the inhibition of the development of WEHI 22.1 cancerous cells injected into Balb/C mice.

The conjugates prepared according to the invention exhibit a specificity of action which is such that it is possible to envisage their use in human therapy for the treatment of cancer. They are prepared for use by injection and can be used either by themselves or in association with another cancer treatment.

TABLE I

| Designation of the test | Expression of the activity | Ricin | A chain | $(A)_p$ chain | Activity ratio of ricin/A chain | Activity ratio of ricin/$(A)_p$ chain |
|---|---|---|---|---|---|---|
| Test 1 | IC 50 in mols/liter | $3 . 10^{-10}$ | $1.3 . 10^{-10}$ | $1.3 . 10^{-10}$ | 0.43 | |
| Test 2 (note 1) | IC 50 in mols/liter | $4 . 10^{-11}$ | $5 . 10^{-8}$ | $68.6 . 10^{-8}$ | 1250 | 17150 |
| Test 3 | Minimum hemagglutinant concentration in mols/liter | $4.2 . 10^{-8}$ | $8.4 . 10^{-5}$ | | 2000 | |
| Test 4 | | $3.3 . 10^{-9}$ | $1.3 . 10^{-6}$ | | 400 | |
| Test 5 (note 2) | LD 50 in mcg/animal | 0.25 | 450 | | 1800 | |

(note 1): These results were obtained on HeLa cells which did or did not carry the hapten TNP.
(note 2): By the intraperitoneal injection of 0.5 ml of an isotonic solution into Charles River France mice of the CD-1 strain (mean weight 20.3 g)

We claim:

1. Process for the preparation of a cytotoxic product having a covalent disulphide bond between a cytotoxic compound and an antibody, the process comprising forming a disulphide bridge between the A chain of ricin and the antibody, the antibody being an immunoglobulin or an immunoglobulin fragment and being specific for a given antigen carried by the cells which are to be destroyed.

2. Process as claimed in claim 1, wherein a compound of the formula $P_1$-SH is reacted with a compound of the formula $P_2$-S-S-X in accordance with the equation: $P_1SH + P_2\text{-S-S-X} \rightarrow P_1\text{-S-S-}P_2 + XSH$, in which when $P_1$ is the radical of the A chain of ricin to which the free thiol group of this molecule is fixed, $P_2$ is an immunoglobulin or an immunoglobulin fragment, or conversely when $P_1$ is an immonoglobulin or an immunoglobulin fragment, $P_2$ is the radical of the A chain of ricin, and X is an organic activator radical.

3. Process as claimed in claim 2, wherein $P_1$ is an immunoglobulin or an immunoglobulin fragment into which a free thiol group is to be introduced, the recognition site of the said immunoglobulin or immunoglobulin fragment is first blocked by prior treatment with the antigen, or with another antigen exhibiting a cross-reaction, or with a hapten, the immunoglobulin or immunoglobulin fragment, protected in this way, then being reacted with δ-acetylmercaptosuccinic anhydride, the thiol groups are liberated by the action of hydroxylamine, and the recognition site is finally unblocked by removing the antigen or hapten.

4. Process as claimed in claim 2, wherein $P_2SH$ represents the A chain of ricin, and the latter is converted into the disulphide by the exchange reaction:

$$P_2SH + X\text{-S-S-X} \rightleftharpoons P_2\text{-S-S-X} + XSH$$

in which X represents an activator radical selected from the pyrid-2-yl or pyrid-4-yl group which is optionally substituted by one or more alkyl, halogen or carboxylic acid groups phenyl, or phenyl which is substituted by one or more nitro or carboxylic acid groups, and the reaction is carried out with a large molar excess of the reagent XSSX, which is removed at the end of the reaction by dialysis or filtration on a molecular sieve in gel form.

5. Process as claimed in claim 3, wherein all the reactions are carried out at pH 7.0 in a phosphate buffer and at ambient temperature.

6. Process as claimed in claim 2, wherein $P_1SH$ represents the A chain of ricin and $P_2$ represents the immunoglobulin or a fragment thereof, and $P_2$ is converted into the activated disulphide in accordance with the equation:

$$P_2 + Y\text{-}R\text{-}S\text{-}S\text{-}X \rightarrow P_2\text{-}R\text{-}S\text{-}S\text{-}X$$

in which Y represents a functional group which is capable of covalently bonding to any one of the functional groups carried by the side chains of the constituent aminoacids of the immunoglobulin, R represents a group $-(CH_2)_n-$, n being an integer from 2 to 10, or a group $$R_3-\underset{|}{CH}-\underset{|}{CH}-R_4,$$

$R_4$ denoting a hydrogen atom or an alkyl group of 1 to 8 C atoms, and $R_3$ denoting a substituent which is inert towards the reactants subsequently used, the reaction being carried out in the homogeneous liquid phase and at ambient temperature.

7. Process as claimed in claim 2, wherein after all the reactions are complete, the conjugate obtained is purified, in order to remove the unreacted compound $P_2$-S-S-X therefrom.

8. A cytotoxic product, consisting in compounds called "conjugates", wherein the A chain of ricin is coupled by a disulphide bridge to a protein structure which is an antibody, the protein structure being capable of selectively recognising an antigen presented at the surface of the carrier cells and the antibody being an immunoglobulin or an immunoglobulin fragment.

9. A product as claimed in claim 8, wherein the antibody is an anti-DNP antibody.

10. A product as claimed in claim 8, wherein the antibody is the $F(ab)'_2$ fragment of the anti-DNP antibody.

11. A product as claimed in claim 8, wherein the antibody is the anti-Thy 1.2 IgM.

12. Process according to claim 7 in which the unreacted compound is removed by fractional precipitation with a water-miscible organic solvent.

13. Process according to claim 7 wherein the unreacted compound is removed by gel permeation chromatography.

14. Process according to claim 7 wherein the unreacted compound is removed by affinity chromatography.

* * * * *